United States Patent
Abbott et al.

(10) Patent No.: US 9,592,300 B2
(45) Date of Patent: Mar. 14, 2017

(54) METHODS OF USING REDOX-ACTIVE SURFACTANTS TO CONTROL POLYMER INTERACTIONS

(75) Inventors: Nicholas L. Abbott, Madison, WI (US); David M. Lynn, Middleton, WI (US); Yukishige Kondo, Nishi-Tokyo (JP); Christopher M. Jewell, Madison, WI (US); Melissa E. Hays, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 2170 days.

(21) Appl. No.: 11/450,640

(22) Filed: Jun. 9, 2006

(65) Prior Publication Data

US 2006/0287270 A1 Dec. 21, 2006

Related U.S. Application Data

(60) Provisional application No. 60/688,935, filed on Jun. 9, 2005.

(51) Int. Cl.

| | |
|---|---|
| *C12N 15/00* | (2006.01) |
| *A61K 47/48* | (2006.01) |
| *A61K 31/295* | (2006.01) |
| *A61K 31/555* | (2006.01) |
| *A61K 48/00* | (2006.01) |
| *C12N 15/88* | (2006.01) |

(52) U.S. Cl.
CPC ........ *A61K 47/4803* (2013.01); *A61K 31/295* (2013.01); *A61K 31/555* (2013.01); *A61K 48/0008* (2013.01); *A61K 48/0025* (2013.01); *A61K 48/0041* (2013.01); *C12N 15/88* (2013.01)

(58) Field of Classification Search
None
See application file for complete search history.

(56) References Cited

PUBLICATIONS

Singh et al., Proc. Natl. Acad. Sci. USA, 2000, 97: 811-816.*
Sakai et al., Colloids and Surfaces A, Jan. 24, 2004, 232: 221-22.*
Saji et al., J. Amer. Chem. Soc., 1985, 107: 6865-6868.*
Vekris et al., J. Gene Med., 2000, 2: 89-96, Abstract.*
Tsuchiya et al., Langmuir, 22003, 19: 9343-9350.*
Miwa et al., Hepatogastroenetrology, 1999, 46: 825-829; Abstract.*
Vekris et al., J. Gene Med., 2000, 2: 89-96.*
Abbott, N, et al., J. Am. Chem. Soc, 2005, 127:11576-11577.
Balakirev, M., et al., Chemistry & Biology 2000, vol. 7, No. 10.
Guo, X. and Szoka, F., Acc Chem. Res. 2003, 36:335-341.
Jewell, C.M., et al., Journal of Controlled Release, 2006, 112:129-138.
Kakizawa, Y., et al., Langmuir, 2001, 17:8044-8048.
Wetzer, B., et al., Biochem J., 2001, 356:747-756.
International Search Report in PCT/US06/022350 date of mailing Dec. 13, 2006.
Skaife, J.J; Abbott, N.L. Langmuir 2000, 16, 3529.
Zhang, et al., Journal of Controlled Release 2004, 100, 165-180.
Shum, et al. Adv Drug Deliv Rev 2001, 53, 273-284.
Budker, et al., Nature Biotechnology 1996, 14, 760-764.
Reddy, et al., J Control Release 2000, 64, 27-37.
Tang, et al., Biochemical and Biophysical Research Communications 1998, 242, 141-145.
Huang, et al., Molecular Therapy 2005, 11, 409-417.
Meers, Adv Drug Deliv Red 2001, 53, 265-272.
Prata, et al., J Am Chem Soc 2004, 126, 12196-7.
J Am Chem Soc 2005, 127, 11576-7.
Kakizawa, et al., Langmuir 1996, 12, 921-924.
Saji, et al., Journal of the American Chemical Society 1991, 113, 450-456.
Hays, et al., Langmuir 2005, 21, 2007-12015.
Zuhorn, I.S. and Hoekstra, D.J. Membrane Biol. 189, 167-179, 2002.
Cotten et al., Methods Enzym. 217:618, 1993.
Fire et al., Nature 391:806-811, 1998.
Gilmore et al., Journal of Drug Targeting 12:315-340.
Crooke "Molecular Mechanisms of Action of Antisense Drugs" Biochim. Biophys. Acta 1489(1):31-44, 1999.
Crooke "Evaluating the Mechanism of Action of Antiproliferative Antisense Drugs", Antisense Nucleic Acid Drug Dev. 10(2):123-126, discussion 127, 2000.
Chan et al., J. Mol. Med. 75(4):267-282, 1997.
Computer Physics Communications 1982, 27, 213-227.
S.W. Provencher, Contin: "A General Purpose Constrained . . . ", Computer Physics Communications 1982, 27, 229-242.
E. Wagner, M. Orgis, W. Zauner, Polylysine-based transfection systems utilizing receptor-mediated delivery Adv Drug Deliv, Rev 1998, 30, 97-113.

* cited by examiner

*Primary Examiner* — Ileana Popa
(74) *Attorney, Agent, or Firm* — Boyle Fredrickson, S.C.

(57) ABSTRACT

The present invention provides methods utilizing redox-active surfactants to provide electrochemical control over polymer interactions. In one embodiment, the invention is directed to a transfection method using a redox-active transfection agent that preferentially promotes transfection dependent on the oxidation state of the transfection agent. Accordingly, certain methods according to the invention provide spatial and/or temporal control of cell transfection.

19 Claims, 13 Drawing Sheets

(a)

(b)

A

B

METHODS OF USING REDOX-ACTIVE SURFACTANTS TO CONTROL POLYMER INTERACTIONS

CROSS REFERENCE TO RELATED APPLICATION

This non-provisional application claims the benefit of U.S. Provisional application 60/688,935, filed Jun. 9, 2005, which is incorporated herein by reference in its entirety.

STATEMENT REGARDING FEDERALLY SPONSORED RESEARCH

This invention was made with United States government support awarded by the National Science Foundation Grant 0327489. The United States has certain rights in this invention.

FIELD OF THE INVENTION

This invention relates generally to the field of polymer/surfactant interactions. More particularly, the present invention is directed to methods of using redox-active surfactants to provide electrochemical control over interactions among and between polymers and surfactants.

BACKGROUND OF THE INVENTION

At present, a broad challenge that confronts the field of gene delivery is the development of synthetic materials that permit the delivery of DNA to cells with spatial and temporal control. Materials that provide such control could be useful as tools for basic biological and biomedical research as well as in applications such as tissue engineering and the development of gene-based therapies. Cationic lipids have been investigated widely for gene delivery because they aggregate with DNA to form lipid/DNA complexes (lipoplexes) that transport DNA into cells (Zhang, et al. *J Control Release* 2004, 100, 165-80; Kabanov, et al. *Self-Assembling Complexes for Gene Delivery: From Laboratory to Clinical Trial*. John Wiley and Sons: New York, 1998). However, conventional lipoplexes are generally active (and thus able to transfect cells) beginning from the time at which they are first formed. As a result, maintaining spatial and temporal control over the transfection of a subset of cells within a larger population presents a significant challenge. The design of functional lipids that permit the localized activation of lipoplexes that are otherwise inactive (and thus do not transfect cells) would make possible new approaches to the delivery of DNA with both spatial and temporal control (Guo, et al., *Accounts of Chemical Research* 2003, 36, 335-341; Shum, et al., *Adv Drug Deliv Rev* 2001, 53, 273-84).

Several past investigations have reported on the design of lipids that respond to local variations in the intracellular environment (e.g., changes in pH, Guo, et al., *Accounts of Chemical Research* 2003, 36, 335-341; Budker, et al., *Nature Biotechnology* 1996, 14, 760-764; Reddy, et al., *J Control Release* 2000, 64, 27-37 reducing potential, Guo, et al., *Accounts of Chemical Research* 2003, 36, 335-341; Tang, et al., *Biochemical and Biophysical Research Communications* 1998, 242, 141-145; Huang, et al., *Molecular Therapy* 2005, 11, 409-417 or the presence of enzymes Guo, et al., *Accounts of Chemical Research* 2003, 36, 335-341; Meers, *Adv Drug Deliv Rev* 2001, 53, 265-72; Prata, et al., *J Am Chem Soc* 2004, 126, 12196-7) that expose latent functionality or 'activate' a lipid toward a specific secondary function. The design of these lipids has been driven largely by the need for DNA delivery agents that address specific and important intracellular barriers to transfection (Guo, et al., *Accounts of Chemical Research* 2003, 36, 335-341). However, because the transformation of these lipids is designed to occur in the intracellular environment, the timing and the location of the 'activation' of these lipids is under cellular control. However, these previous approaches do no achieve localized activation of lipids and lipoplexes using externally controlled stimuli.

In a recent communication, Abbott, et al. reported the results of an investigation to determine the ability of a two-tailed ferrocene-containing cationic lipid, bis(11-ferrocenylundecyl)dimethylammonium bromide to interact with DNA and transfect mammalian cells (*J Am Chem Soc* 2005, 127, 11576-7, incorporated by reference herein in its entirety). The structure of BFDMA is shown in FIG. 1 and has been previously described (Kakizawa, et al., *Langmuir* 1996, 12, 921-924; Kakizawa, et al., *Langmuir* 2001, 17, 8044-8048).

Beyond the gene delivery context, several groups have observed that redox-active amphiphiles are capable of achieving active electrochemical control over various surfactant/polymer properties in aqueous systems (e.g., Saji, et al., *Journal of the American Chemical Society* 1991, 113, 450-456)). Recently, Hays et al. demonstrated that the cationic surfactant 11-(ferrocenylundecyl)trimethylammonium bromide (FTMA, structure shown in FIG. 1), when combined with electrochemical methods, can be used to control interactions between the surfactant and a synthetic polymer in aqueous solution (Hays, et al., *Langmuir* 2005, 21, 2007-12015, incorporated by reference herein in its entirety). The ability to control the physical properties of polymers in solution would find broad applicability in the manipulation of polymer size, rheological properties, aggregation state, gelation, optical appearance, electrical properties, and phase behavior.

At present, there exists a need for improved materials and methods to achieve active spatial and temporal control over the delivery of nucleic acids to cells in the context of transfection. As well, the technology to control the physical properties of polymers in solution would find broad applicability in industrial applications where, for example, polymer aggregation state or optical appearance are critical parameters.

SUMMARY OF THE INVENTION

In general, the present invention provides methods of controlling interactions among and between polymers and surfactants. Such methods include steps of contacting a polymer with a redox-active surfactant that is transformable between (i) a first oxidation state and (ii) a second oxidation state wherein the interaction of polymer and surfactant depends on the oxidation state of the surfactant.

In certain embodiments, the present invention provides methods to control the aggregation of polymers and surfactants in solution. Such methods include steps of: (a) providing a redox active surfactant transformable between: (i) a first oxidation state that facilitates polymer aggregation; and (ii) a second oxidation state that changes the nature of the polymer aggregation. The redox active surfactant in the first oxidation state is contacted with polymer in order to change the state of aggregation of the polymer.

The redox-active surfactant can be non-ionic, anionic, net anionic, zwitterionic, cationic, or net cationic. The surfactant is preferably cationic, more preferably a cationic surfactant bearing one or more redox-active groups. A preferred redox-active group is a ferrocenyl moiety. Methods of changing the interactions of surfactants and synthetic and natural polymers (e.g., nucleic acids (including DNA and RNA), proteins, peptides, polysaccharides) are preferred with methods related to aggregation of nucleic acid useful in the transfection context being most preferred.

Accordingly, the present invention provides certain embodiments directed to transfection methods. Such methods include steps of: (a) providing a redox active surfactant transformable between: (i) a first oxidation state that facilitates transfection; and (ii) a second oxidation state that is less effective at facilitating transfection. The redox active surfactant in the first oxidation state is contacted with a cell and nucleic acid in order to facilitate transfection of the cell with the nucleic acid.

In certain embodiments, the oxidation state of the redox active surfactant is controlled by application of an electrical current to the surfactant. This current may be supplied by, for example, an electrode such that spatial and/or temporal control over transfection is achieved.

The present invention also provides methods based on ferrocene-containing molecules to deliver macromolecules and small molecules to cells. Such methods include steps of: (a) providing a ferrocene containing molecule: and (b) contacting cells with the ferrocene-containing molecules and macromolecules or small molecules.

In yet another embodiment, the present invention also provides methods to control the aggregation of polymers in solution. Such methods include steps of: (a) providing a redox active surfactant transformable between: (i) a first oxidation state that facilitates polymer aggregation; and (ii) a second oxidation state that is less effective at facilitating polymer aggregation. The redox active surfactant in the first oxidation state is contacted with polymers in order to change the state of the polymers, including but not limited to their size (e.g., hydrodynamic size, molecular weight of aggregate), their rheological properties, their state of aggregation, gelation, optical appearance, their electrical properties, their phase behavior (such as clouding temperature) and their thickness.

In a related embodiment, the present invention provides methods to control the interactions of proteins and surfactants in solution. Such methods include steps of: (a) providing a redox active surfactant transformable between: (i) a first oxidation state that facilitates protein-surfactant interaction; and (ii) a second oxidation state that is less effective at facilitating protein-surfactant interaction. The redox active surfactant in the first oxidation state is contacted with proteins in order to control the state of the protein, including but not limited to protein binding activity, protein aggregation, denaturation, protein secondary and tertiary structure, enzymatic activity, and protein crystallization.

Other objects, features and advantages of the present invention will become apparent after review of the specification, claims and drawings.

Experiments were conducted in OptiMEM with exposure times of A) 2 hours, B) 4 hours, and C) 12 hours.

Figure 13:
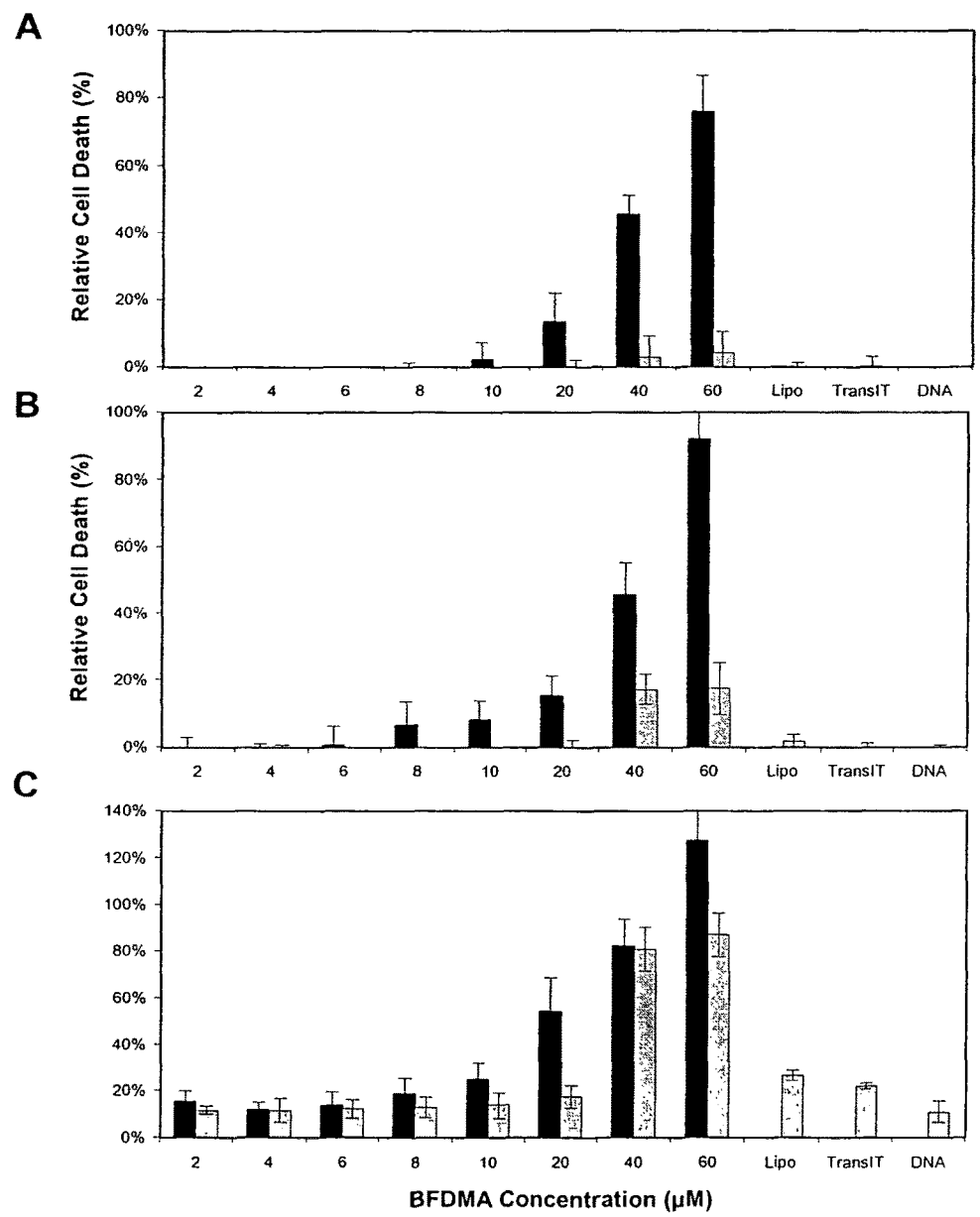
FIG. 13. Cytotoxicity of reduced BFDMA (black), oxidized BFDMA (grey), and commercial transfection agents (Lipofectamine 2000 or TransIT-LT1) in COS-7 cells.
Figure 14:
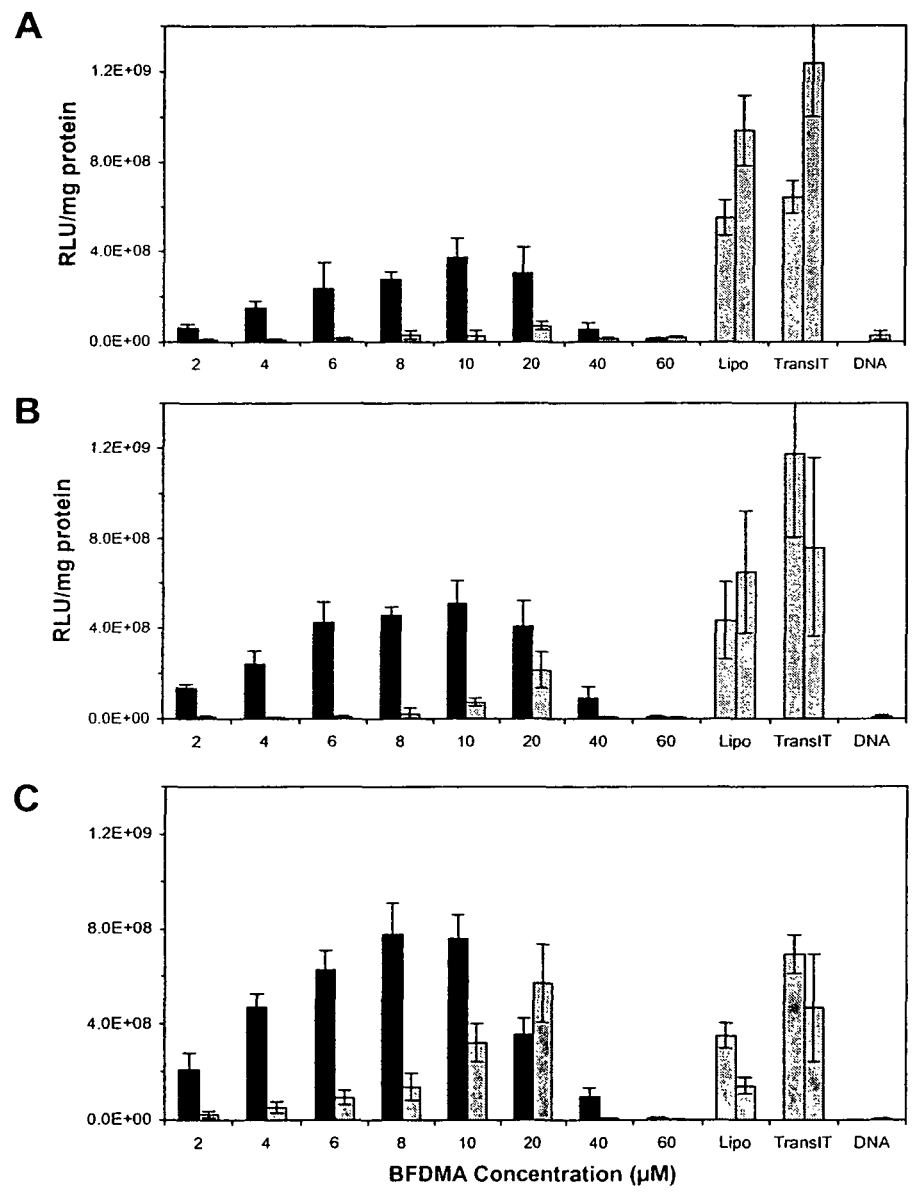

FIG. 14. Normalized luciferase expression using reduced BFDMA (black), oxidized BFDMA (grey), and commercial transfection agents (Lipofectamine 2000 or TransIT-LT1) in COS-7 cells. Experiments conducted with BFDMA were performed in OptiMEM with exposure times of A) 2 hours, B) 4 hours, and C) 12 hours and data correspond to the cytotoxicity data shown in FIG. 13. Values shown for control experiments using Lipofectamine 2000 or TransIT-LT1 were conducted in serum-containing medium (left) and serum-free medium (right) according to the manufacturers' optimized protocols.

Figure 15:
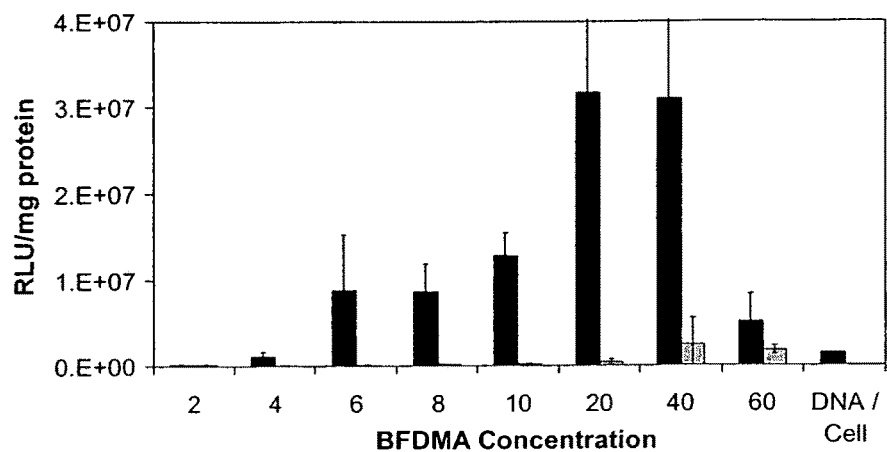

FIG. 15. Normalized luciferase expression in COS-7 cells transfected with p-CMVLuc and using reduced BFDMA (black) or oxidized BFDMA (grey). Experiments were conducted in DMEM with an exposure time of 4 hours.

Figure 16:
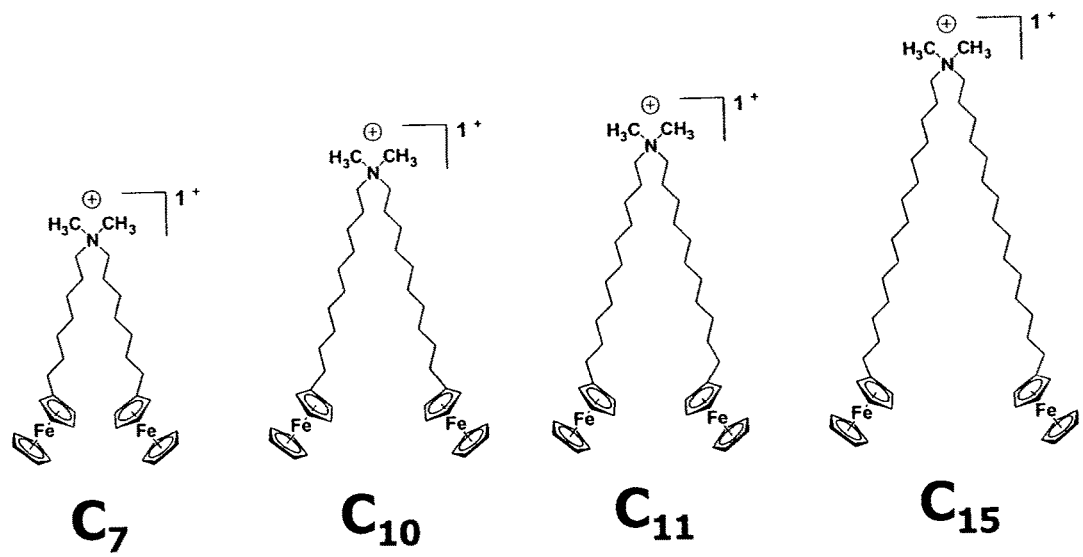

FIG. 16. Structures of four n-alkylferrocenyl lipids ({Fc $(CH_2)_n$}$_2N^+(CH_3)_2Br^-$ (n-BFDMA; n=7, 10, 11, 15)).

Figure 17:
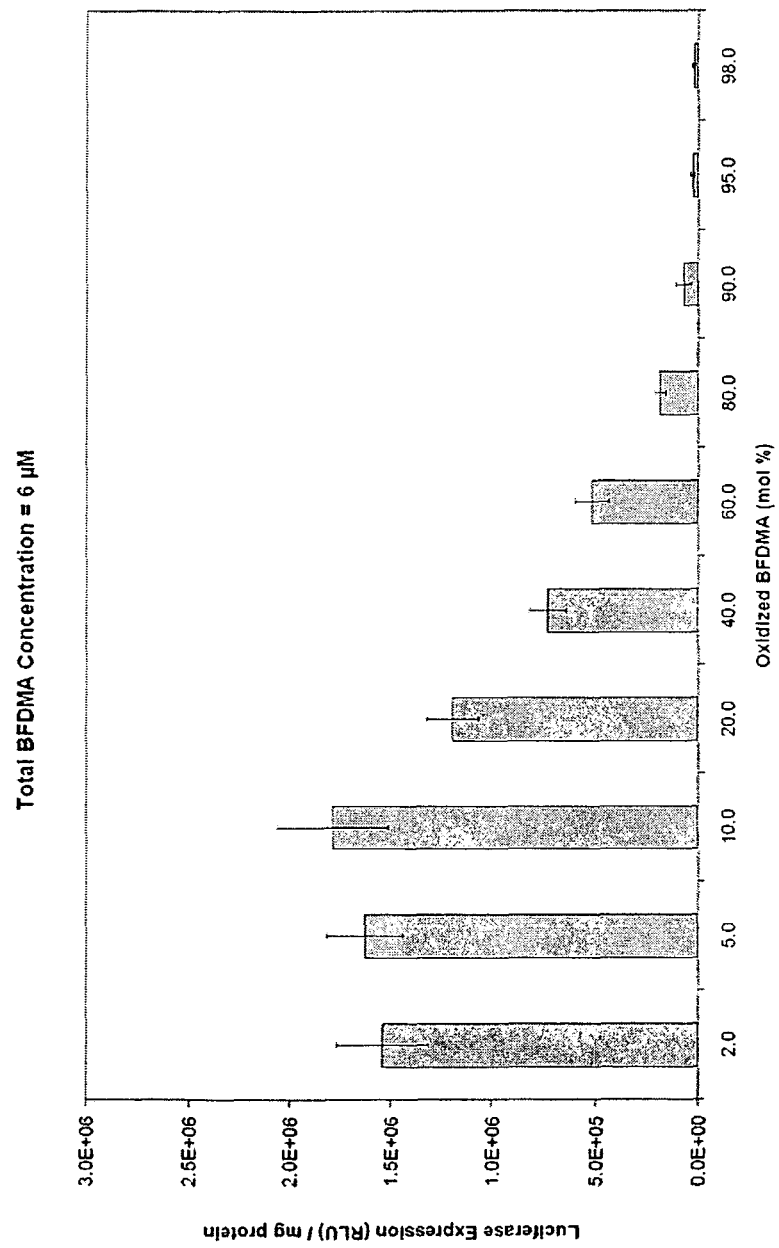

FIG. 17. Luciferase expression in COS-7 cells exposed to lipoplexes formed from pCMV-Luc and mixtures of reduced and oxidized BFDMA.

Figure 18:
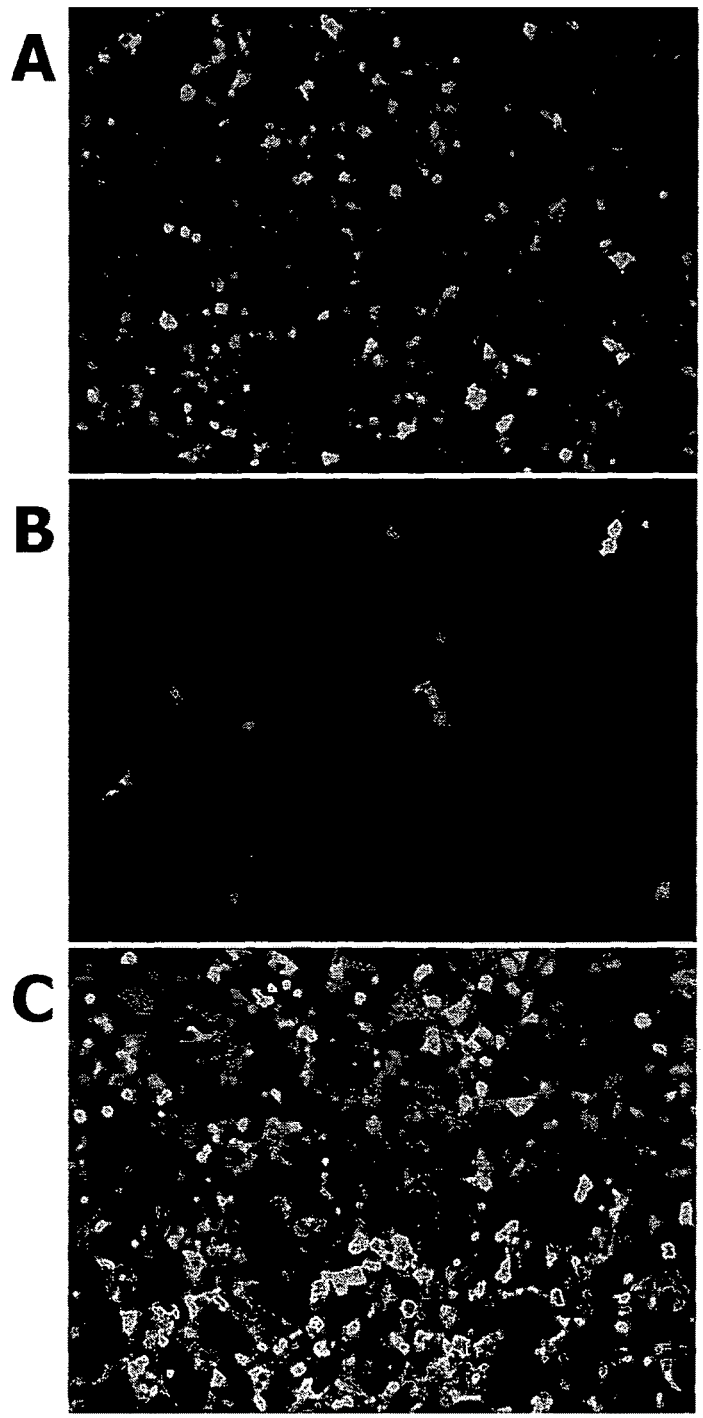

FIG. 18. Data demonstrating BFDMA retains transfection activity following electrochemical cycling. EGFP expression in COS-7 cells exposed to lipoplexes formulated from A) pEGFP and reduced BFDMA, B) pEGFP and oxidized BFDMA, and C) pEGFP and BFDMA that was oxidized and subsequently reduced prior to being contacted with DNA.

Figure 19:
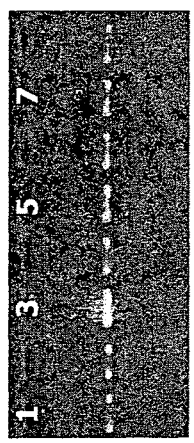
Figure 19:
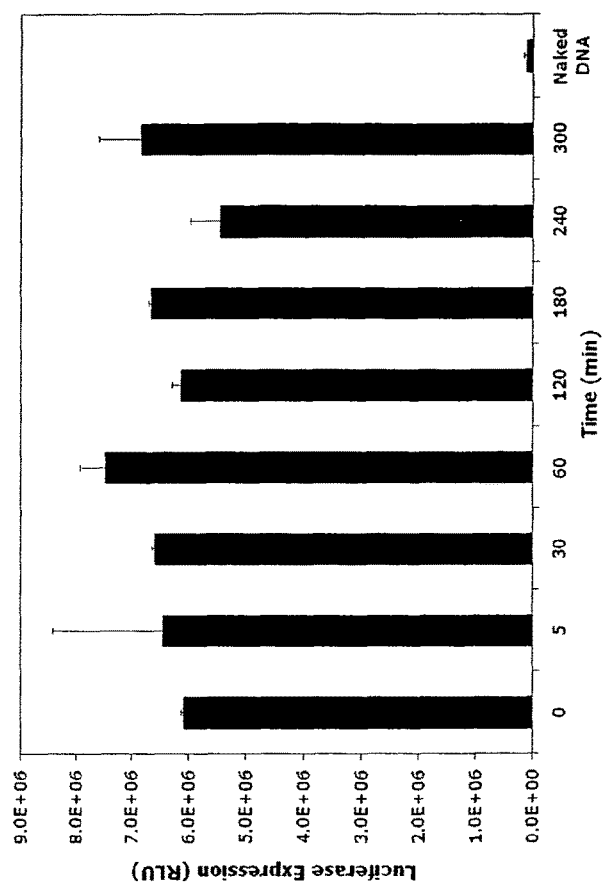

FIG. 19. Agarose gel electrophoresis characterization of DNA and corresponding expression of same DNA in cells COS-7 cells as a demonstration of the DNA's structural and biological integrity after exposure to electrical potential.

DETAILED DESCRIPTION OF THE INVENTION

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

In general, the present invention provides methods of controlling interactions among and between polymers and surfactants. Such methods include steps of contacting a polymer with a redox-active surfactant that is transformable between (i) a first oxidation state and (ii) a second oxidation state wherein the interaction of polymer and surfactant depends on the oxidation state of the surfactant.

In certain embodiments, the present invention provides methods to control the aggregation of polymers and surfactants in solution. Such methods include steps of: (a) providing a redox active surfactant transformable between: (i) a first oxidation state that facilitates polymer aggregation; and (ii) a second oxidation state that is less effective at facilitating polymer aggregation. The redox active surfactant in the first oxidation state is contacted with polymer in order to change the state of aggregation of the polymer.

The redox-active surfactant can be non-ionic, anionic, net anionic, zwitterionic, cationic, or net cationic. As used herein, the term "surfactant" shall refer to a compound that reduces surface tension when dissolved in water or aqueous solutions, or that reduces interfacial tension between two liquids, or between a liquid and a solid. The term surfactant is used in a manner that includes all lipids, amphiphiles or macromolecular surface-active or associating species. The surfactant is preferably cationic, more preferably a cationic surfactant bearing one or more redox-active groups. A preferred surfactant will contain a redox-active group of the ferrocenyl type. Examples of cationic surfactants containing ferrocenyl groups include, but are not limited to: [Fc-$C_n$—$N^+(CH_3)_3$] (FTMA), FPEG Fc-$C_n$—(OCH$_2$CH$_2$)$_n$—OH, [Fc-(CH$_2$)$_n$]$_2$—$N^+(CH_3)_2Br$— (n-BFDMA; where n=7, 10, 11 or 15), Fc-$C_n$—$N^+(CH_3)_2$—$C_n$—$N^+(CH_3)_2$-Fc, Fc-CH$_2$—$N^+(CH_3)_2$—$C_n$, (Ferrocenylmethyl)dimethyloctadecylammonium hexafluorophosphate, Fc-$C_n$, Fc-CH$_2$O—$C_n$, Fc-CH$_2$—$N^+(C_n)_2$, Fc-[$C_n$]$_2$, Fc-[$C_n$—$N^+(CH_3)_3$]$_2$, Fc-[CH$_2$O—$C_n$]$_2$, Fc-[CO—$C_n$]$_2$, Fc-[COO—$C_n$]$_2$, Fc-[CONH—$C_n$]$_2$, Fc-[CO—N($C_n$)$_2$]$_2$, Fc-[COO-cholestanyl]$_2$, N-ferrocenoylhexadecamide-O-sulfato-L- serine sodium salt (FS), 16-ferrocenylhexadecanoic acid. The molecules (11-ferrocenylundecyl)trimethylammonium bromide (FTMA) and bis-(11-ferrocenylundecyl)dimethyl ammonium bromide (BFDMA) are especially preferred.

The term "polymer" shall generally refer to macromolecules formed by the chemical union of subunits called monomers. The number of monomers may not be exactly known (e.g., in pure cellulose) in naturally-occurring polymers, also termed biopolymers. In synthetic polymers, this number can be controlled to a predetermined extent, e.g., by capping agents. The present invention is applicable to polymers of natural, synthetic, or semisynthetic origin. Examples of natural polymers include polysaccharides (e.g., starch or cellulose), polypeptides, polynucleotides, or hydrocarbons (e.g., polyisoprene). Application of the present invention to polynucleotides is described in further detail below. Synthetic polymers include thermoplastic and thermosetting polymers including, but not limited to, polystyrene, polypropylene, polyethylene, or polyesters and derivatives thereof. As well, polymers may be of semisynthetic origin including, but not limited to, cellulosics (e.g., rayon or methyl cellulose derivatives) or modified starches (e.g., starch acetate). Methods of changing the interactions of surfactants and synthetic and natural polymers (e.g., nucleic acids, proteins, peptides, polysaccharides) are preferred with methods related to aggregation of nucleic acid useful in the context of transfection being most preferred.

Accordingly, the present invention provides certain embodiments directed to transfection methods. Such methods include steps of: (a) providing a redox active surfactant transformable between: (i) a first oxidation state that facilitates transfection; and (ii) a second oxidation state that is less effective at facilitating transfection. The redox active surfactant in the first oxidation state is contacted with a cell and nucleic acid in order to facilitate transfection of the cell with the nucleic acid. As used herein, the term "transfection" shall refer generally to a method by which nucleic acid is introduced or delivered into a cell, particularly a eukaryotic cell, in a manner that promotes the downstream biological and intracellular processing of the nucleic acid. Transfection methods presently disclosed are preferably performed using cloned nucleic acid in the form of DNA containing coding sequences and control regions (e.g., promoters) in order to facilitate expression and/or replication of the nucleic acid. The term "transfection" as used herein shall also encompass the delivery of RNA and siRNA into cells. In certain embodiments related to transfection, a helper lipid is provided in combination with the above-described polymer to increase efficiency of transfection. Various helper lipids are known to the artisan and have been described (e.g., see Zuhorn, I. S. and Hoekstra, D. *J. Membrane Biol.* 189, 167-179, 2002).

As an exemplary embodiment, the ability of the redox-active, ferrocene-containing cationic lipid bis(11-ferrocenylundecyl)dimethylammonium bromide (BFDMA)] to transfect mammalian cells is described in the example section below. The data provided demonstrate a range of conditions over which this lipid was capable of transfecting cells and how the oxidation state of the ferrocenyl groups in this material was useful to influence the extent of transfection. Experiments conducted in the COS-7 cell line using BFDMA and reporter plasmids encoding enhanced green fluorescent protein (EGFP) and firefly luciferase demonstrated that BFDMA was able to transfect cells. The extent of transfection depended significantly upon both the concentration of BFDMA and the oxidation state of the lipid. Quantitative characterization of cytotoxicity and gene expression demonstrated that a window of concentration existed over which reduced BFDMA was non-cytotoxic and yielded high levels of transfection, but over which electrochemically oxidized BFDMA yielded very low (background) levels of transfection. Characterization of lipoplexes using dynamic light scattering demonstrated that reduced and oxidized BFDMA formed small aggregates (ca. 90 nm to 250 nm) at concentrations of lipid ranging from 2 µM to 10 µM. Taken together, these results demonstrate that the oxidation state of BFDMA, which can be controlled electrochemically, can be used to control the extent of cell transfection. These results provide the artisan with guidelines for transfection procedures that exploit the redox behavior of ferrocene-containing lipids to achieve active spatial and temporal control over transfection using electrochemical methods. The present invention therefore combines the ability of cationic lipids to aggregate with nucleic acids and transfect cells with the ability to control the charge density of ferrocene-containing lipids using electrochemical methods.

Certain embodiments of the invention relate to methods that provide for temporal control over the delivery of DNA in vivo. In one example, an implantable device is engineered such that an electrical potential can be applied. Application of an electrochemical potential results in the transformation of an electroactive transfection agent from a state that does not facilitate desirable levels of transfection to a state that facilitates substantially high and desirable levels of transfection. The electrode can be engineered such that this transformation occurs in either the interstitial space of a tissue or in the lumen of a vessel or organ. As used herein, the term "electrode" shall refer generally to an electrical conductor through which an electric current enters or leaves a medium comprising a redox active agent wherein the electrode is capable of oxidizing/reducing the redox active agent. In a specific embodiment, the implantable device is a stent or an electrode surface placed in a blood vessel and in contact with blood. Application of an electrical potential to the device results in the electrochemical transformation or activation of transfection agent circulating in the blood. The transfection agent is rapidly transported throughout the circulatory system, leading to temporal control over the delivery of DNA. As would be apparent to one of ordinary skill in the art, this embodiment does not require that the electrochemical transformation of the transfection agent occur in the presence of DNA. As would further be apparent to one of skill in the art, the transfection agent can be modified structurally so as to lead to targeted delivery or the transfection of a specific tissue or cell type.

Other embodiments of the invention involve the placement of an electrode in the interstitial space of a tissue or organ to achieve temporal and/or spatial control over transfection. Application of an electrochemical potential results in the transformation of an electroactive transfection agent present in the interstitial space from a state that does not facilitate desirable levels of transfection to a state that facilitates substantially high and desirable levels of transfection. As would be apparent to one of skill in the art, this embodiment provides temporal control over transfection and does not require that the electrochemical transformation of the transfection agent occur in the presence of DNA. By application of an electrical potential to an electrode placed in a specific and desired location, transfection can be localized spatially to those cells and tissues in contact with or located in the vicinity of the electrode. As used herein, the term "tissue" shall refer to an aggregation of morphologically and functionally similar cells regarded as a collective entity. If the electrode is fabricated to be small compared to the volume of the space containing the DNA present, spatial control is exerted over the delivery of the DNA to cells. If the electrode is fabricated to be smaller than or similar in size to the dimensions of a cell, the delivery of DNA can be restricted spatially to a single cell or small clusters of cells. If the electrode is fabricated to be cylindrical or tube-shaped, the application of an electrical potential results in the spatial transfection of cells in three-dimensions as dictated by the shape and dimensions of the electrode and the contour of the electrode surface. As would be apparent to one of ordinary skill in the art, the electrode can be fabricated in any number of desirable shapes and dimensions. The examples provided above are not limiting. In some embodiments, the electrode is placed permanently in the tissue or organ. In other embodiments, the electrode may be removed and subsequently replaced or relocated to another location to induce transfection in a different location.

Yet other embodiments of the invention combine the electroactive transfection agent with an agent that facilitates the transfer of electrons to or from an electron donor or acceptor and to or from an electroactive transfection agent. In one embodiment, the agent is a protein or enzyme. In a specific example of this embodiment, the presence of glucose oxidase facilitates the transfer of electrons from glucose to an electroactive transfection agent, leading to the onset of transfection. In a second example, the agent is a photosensitizer that facilitates electron transfer to or from the electroactive transfection agent. In this embodiment, the onset and specific location of transfection occurs upon illumination with light.

Further embodiments of the invention involve the transformation of a redox-active transfection agent from a state that does not facilitate desirable levels of transfection to a state that facilitates substantially high and desirable levels of transfection by virtue of exposure to the oxidative or reductive environments within a particular tissue or organ. In one specific embodiment, a transfection agent that is not active in the reduced state is transformed to an active state upon exposure to an oxidative environment, such as may be found in certain tumor tissues. In this example, transfection may be localized spatially to the tumor site. In an alternative embodiment, transformation of a transfection agent to a reduced state may be accomplished by exposing the agent to a reductive environment such as, for example, the reductive environment provided by exposure to glutathione. The reduction of an oxidized agent by glutathione is described in the examples section below.

Yet other embodiments of the invention involve spatial patterning of transfection within a population of cells in vitro. In one embodiment, cells are grown on a surface. In one particular embodiment, cell culture media containing a DNA construct encoding a desired gene product and the electroactive transfection agent is added to the cells. Placement of an electrode in the vicinity of a subset of the cells leads to the transfection of the subpopulation of cells defined by the placement of the electrode and application of an electrical potential to the electrode. The cell culture media may be replaced with a second media that contains a DNA construct encoding a different gene product and an eletroactive transfection agent. Placement of an electrode in the vicinity of the same or different subset of cells leads to the delivery of the second DNA construct to the subpopulation of cells defined by the location of the electrode. As would be recognized by one of ordinary skill in the art, this embodiment is not limited by the number of DNA constructs that can be delivered, the number or spatial arrangements of specific cell types that can be used, or the geometry or dimensions of the electrode. As would be apparent to one of skill in the art, techniques that permit the patterned transfection of defined sub-populations in two-dimensional arrays of live cells are of current interest in the context of diagnostics and new tools for drug discovery and basic biomedical research. In a particularly useful embodiment, the cells are stem cells. As would be apparent to one of ordinary skill in the art, surfaces useful in this embodiment are not limited to planar surfaces or synthetic materials. In a particularly useful embodiment, the surface is three-dimensional. In another useful embodiment, the surface on which the cells are supported is comprised of cells, the type of which may be the same as or different from the cells that are desired to be transfected.

Nucleic acid delivered by a transfection method according to the invention is preferably in the form of deoxyribonucleic acid (DNA), more preferably in the form of a DNA vector, most preferably an expression vector. Alternatively, the inventive methods may convey ribonucleic acid or, in yet other alternative embodiments, a protein/nucleic acid (PNA) molecule or other mimetic understood by one of skill to be a nucleic acid equivalent. As used herein, the term "nucleic acid" generally refers to any polyribonucleotide or polydeoxribonucleotide, which may be unmodified RNA or DNA or modified RNA or DNA. "Nucleic acids" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "nucleic acid" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "nucleic acid" also includes DNAs or RNAs as described above that contain one or more modified bases. Thus, DNAs or RNAs with backbones modified for stability or for other reasons are "nucleic acids" as that term is intended herein. Moreover, DNAs or RNAs comprising unusual bases, such as inosine, or modified bases, such as tritylated bases, to name just two examples, are nucleic acids as the term is used herein. It will be appreciated that a great variety of modifications have been made to DNA and RNA that serve many useful purposes known to those of skill in the art. The term "nucleic acid" as it is employed herein embraces such chemically, enzymatically or metabolically modified forms of nucleic acids, as well as the chemical forms of DNA and RNA characteristic of viruses and cells, including prokaryotic and eukaryotic cells. "Nucleic acid" also embraces short polynucleotides often referred to as oligonucleotide(s).

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors, referred to above, are termed "expression vectors". In general, expression vectors of utility in the present methods are in the form of plasmids. In the present specification, "plasmid" and "vector" can be used interchangeably as the plasmid is the most commonly used form of vector. However, the invention is intended to encompass the use of other forms of expression vectors, such as viral vectors (e.g., replication defective retroviruses, adenoviruses and adeno-associated viruses), which serve equivalent functions.

Expression vectors useful in the present invention include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence in the host cell. The term "regulatory sequence" is intended to include promoters, enhancers, and other expression control elements (e.g., polyadenylation signals). Such regulatory sequences are known in the art and described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the cell to be transfected, the level of expression of protein desired, and the like.

Methods according to the present invention are suited to deliver nucleic acid to cells in the presence of cell culture medium, as demonstrated in the following examples section. However, as can be appreciated by the foregoing description, the present invention is applicable to the delivery of nucleic acids to cells contained within living tissues, particularly to tissues present within a living subject, preferably a human subject.

In certain embodiments, particularly for delivery of nucleic acids in a living entity, it is desirable to target a nucleic acid to a particular cell or tissue. A variety of agents that can direct a substrate to particular cells are known in the art (see, for example, Cotten et al., *Methods Enzym.* 217: 618, 1993). Examples of useful targeting agents include, but are in no way limited to, low-density lipoproteins (LDLs), transferrin, asiaglycoproteins, gp120 envelope protein of the human immunodeficiency virus (HIV), toxins, antibodies, and carbohydrates.

As well, the present invention encompasses the delivery of nucleic acids that provide the polynucleotide as an antisense agent or RNA interference (RNAi) agent (Fire et al. Nature 391:806-811, 1998; Gilmore et al., Journal of Drug Targeting 12:315-340, 2004; incorporated herein by reference in their entirety and for all purposes as if fully set forth herein). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular Mechanisms of Action of Antisense Drugs" Biochim. Biophys. Acta 1489(1):31-44, 1999; Crooke "Evaluating the Mechanism of Action of Antiproliferative Antisense Drugs" Antisense Nucleic Acid Drug Dev. 10(2):123-126, discussion 127, 2000; Methods in Enzymology volumes 313-314, 1999; each of which is incorporated herein by reference in its entirety and for all purposes as if fully set forth herein). The binding may be by conventional base pair complementarity, or, for example, in the case of binding to DNA duplexes, through specific interactions in the major groove of the double helix (i.e., triple helix formation) (Chan et al. J. Mol. Med. 75(4):267-282, 1997; incorporated herein by reference).

In still another embodiment, the invention provides kits for practice of the methods described herein. In one preferred embodiment directed to transfection, the kits comprise operational instructions and one or more containers containing the redox active transfection agent and necessary stock or working solutions to carry out the transfection method. Kits according to the invention may include instructional materials containing directions (i.e., protocols) for the functional use of the kit, and, optionally, for interpretation of transfection results. Any medium capable of storing instructional materials and communicating them to an end user is contemplated for inclusion in a kit. Such media include, but are not limited to printed media, electronic storage media (e.g., magnetic discs, tapes, cartridges, chips), optical media (e.g., CD ROM), and the like. Such media may include addresses to internet sites that provide such instructional materials.

The present invention also provides methods based on ferrocene-containing molecules to deliver macromolecules and small molecules to cells. Such methods include steps of (a) providing a ferrocene-containing molecule and (b) contacting cells with the ferrocene-containing molecules and macromolecules or small molecules. The terms "macromolecules" and "small molecules" shall include, but not be limited to, a therapeutic molecule, diagnostic molecule, peptide, or carbohydrate, for example a macromolecular carbohydrate such as heparin.

As can be appreciated, the present invention provides methods to control the interactions of polymers in solution. Such methods include steps of: (a) providing a redox active surfactant transformable between: (i) a first oxidation state that facilitates polymer aggregation; and (ii) a second oxidation state that is less effective at facilitating polymer aggregation. The redox active surfactant in the first oxidation state is contacted with polymers in order change the state of the polymers, including but not limited to their size (e.g., hydrodynamic size, molecular weight of aggregate), their theological properties, their state of aggregation, gelation, optical appearance, their electrical properties, their phase behavior (such as clouding temperature) and their thickness.

In certain related embodiments, the present invention provides methods to control the interactions of proteins and surfactants in solution. Such methods include steps of: (a) providing a redox active surfactant transformable between: (i) a first oxidation state that facilitates protein-surfactant interaction; and (ii) a second oxidation state that is less effective at facilitating protein-surfactant interaction. The redox active surfactant in the first oxidation state is contacted with proteins in order to change the state of the proteins, including but not limited to protein binding activity, protein aggregation, denaturation, protein secondary and tertiary structure, enzymatic activity, and protein crystallization.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Electrochemical Control of Interactions of Polymers and Redox-Active Surfactants A. Interactions of FTMA and ethyl(hydroxylethyl) cellulose (EHEC)

Figure 2:
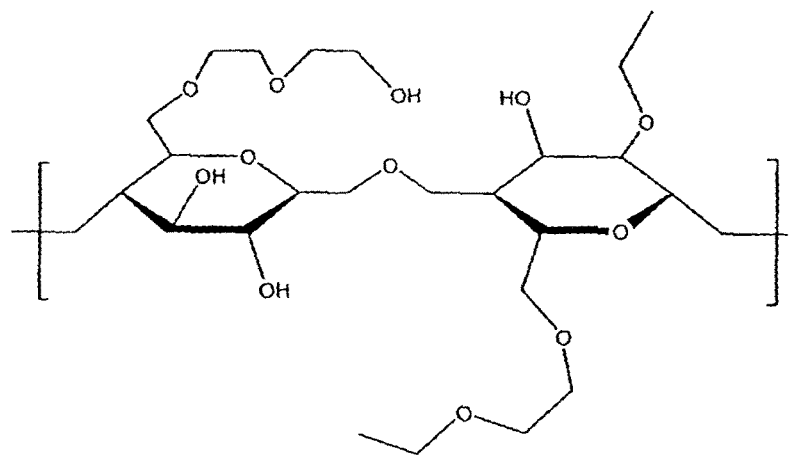
FIG. 2. Molecular structure of ethyl(hydroxylethyl) cellulose (EHEC).
Figure 3:
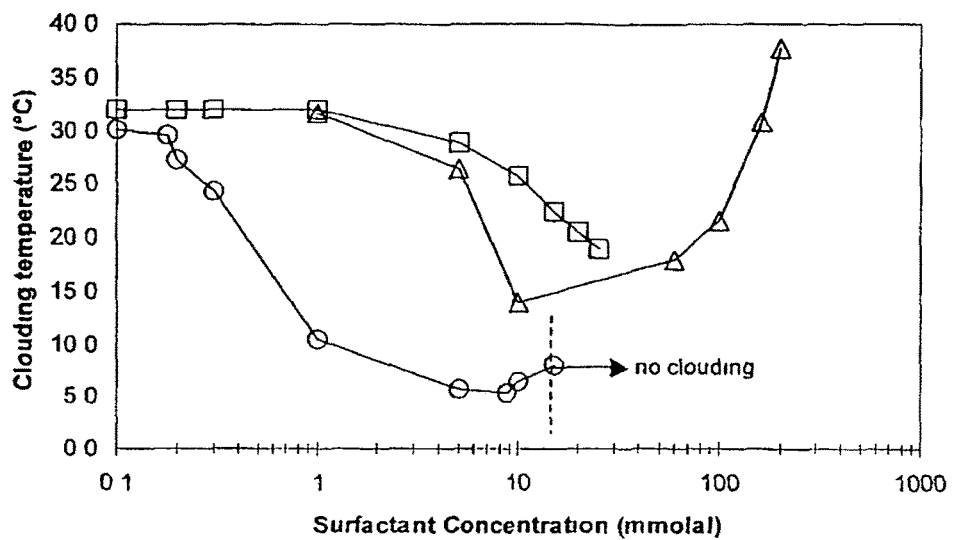
FIG. 3. Clouding temperatures of 0.1% (w/w) EHEC, 0.1M $Li_2SO_4$, with dodecyltrimethyl ammonium bromide (DTAB) (Δ), reduced FTMA (○), and oxidized FTMA (□). No clouding temperatures were reached for reduced FTMA concentrations above 15 mmolal up to 80° C. Lines are only included as a guide.

Surfactant-ethyl(hydroxylethyl) cellulose (EHEC) interactions were characterized by observing the clouding temperature of solutions of EHEC containing various concentrations of surfactant. The structure of EHEC is provided in FIG. 2. FIG. 3 shows the effect of dodecyltrimethyl ammonium bromide (DTAB) on the clouding temperature of 0.1 wt % EHEC in the presence of 0.1M $Li_2SO_4$. In the absence of DTAB, the clouding temperature of the solution of EHEC was 32±0.1° C. At DTAB concentrations near its CMC (10 mM), the cloud point is decreased to 14±0.3° C. At concentrations higher than the CMC, the cloud point increases. These observations are qualitatively similar to EHEC-NaCl-SDS and are consistent with a model in which low concentrations of DTAB promote aggregation of EHEC and thereby lower the cloud point while high concentrations of DTAB disperse these aggregates and thus raise the cloud point of the solution.

Figure 1:
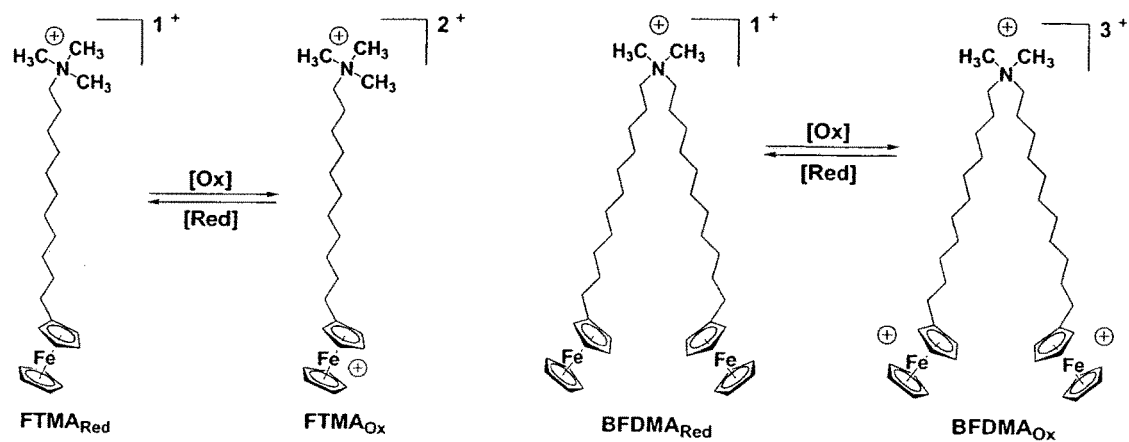
FIG. 1. Structures of the two cationic, ferrocene-containing lipids 11-(ferrocenylundecyl)trimethylammonium bromide (FTMA) and bis(11-ferrocenylundecyl)dimethylammonium bromide (BFDMA) used in this investigation. The charge density of FTMA can be cycled between a +1 state (reduced) and a +2 state (oxidized) by the application of an electrochemical potential. The charge density of BFDMA can be cycled between a +1 state (reduced) and a +3 state (oxidized).

FIG. 3 also shows cloud points of aqueous solutions of reduced and oxidized FTMA in 0.1 wt % EHEC and 0.1M $Li_2SO_4$ as a function of the surfactant concentrations. The solutions containing reduced FTMA show a depression in cloud point at concentrations between 0.2 and 15 mmolal, similar to the DTAB solutions described above. The cloud points of the solutions of reduced FTMA are lower than solutions of DTAB, suggesting that reduced FTMA promotes aggregation of EHEC more strongly than DTAB. The substitution of the terminal methyl group of DTAB with the ferrocene moiety of (11-ferrocenylundecyl)trimethylammonium bromide (FTMA) likely enhances the association of FTMA with EHEC as compared to DTAB. The structure of FTMA is shown in FIG. 1. The cloud point of EHEC is depressed in the presence of lower concentrations of reduced FTMA than of DTAB. This observation is consistent with a model of cooperative interactions between the FTMA molecules and EHEC as the CMC of reduced FTMA in 0.1M $Li_2SO_4$ is 0.1 mM is 100 times lower than the CMC of DTAB.

At concentrations of reduced FTMA above 15 mmolal, the inventors did not measure clouding to occur upon heating the solutions to 80° C. The inventors have measured 16 mmolal reduced FTMA to have a cloud point near 15 mmolal, but 17-25 mmolal solutions exhibit no measurable clouding upon heating to 80° C. This observation suggests the edge of a phase boundary. Aqueous solutions of PEO exhibit closed-loop two-phase regions. Such a two-phase envelope would be consistent with the inventors' observations in the EHEC-FTMA system.

Solutions containing oxidized FTMA behave qualitatively differently from solutions containing DTAB or reduced FTMA. A minimum in the cloud temperature was not observed with increasing concentration of oxidized FTMA. The cloud point decreases monotonically with increasing concentration of oxidized FTMA, similar to that found when adding increasing amounts of $Li_2SO_4$ to dilute EHEC solutions (seen in FIG. 4). This result indicates that EHEC and oxidized FTMA do not interact through a cooperative mechanism. The inventors also noted that the magnitude of the decrease in clouding temperature caused by oxidized FTMA is larger than for a salt solution as $Li_2SO_4$. Comparison of the cloud temperature curves in FIG. 3 reveals that changes in the oxidation state of ferrocene lead to changes in clouding behavior of EHEC in aqueous solution.

To summarize, the cloud point observations of the EHEC-$Li_2SO_4$-surfactant solutions described above lead to three conclusions. First, the clouding behavior of solutions of EHEC in the presence of DTAB is qualitatively similar to SDS and reflects cooperative interactions. Second, reduced FTMA depresses the cloud point of EHEC more than DTAB, indicating that stronger interactions exist between reduced FTMA and EHEC than between DTAB and EHEC. Third and most important, by observing the cloud point curves of solutions containing oxidized and reduced FTMA, the clouding properties of dilute EHEC may be controlled by the oxidation state and concentration of FTMA.

The inventors measured the scattering of light by the samples at five angles. Below, for reasons of space, we provide the autocorrelation functions (ACFs) measured at 75°. The ACFs measured at 75° are representative of those measured at other angles. All of these measurements were performed at 25° C. Solutions with a clouding temperature below 25° C. were not measured by dynamic light scattering.

Figure 5:
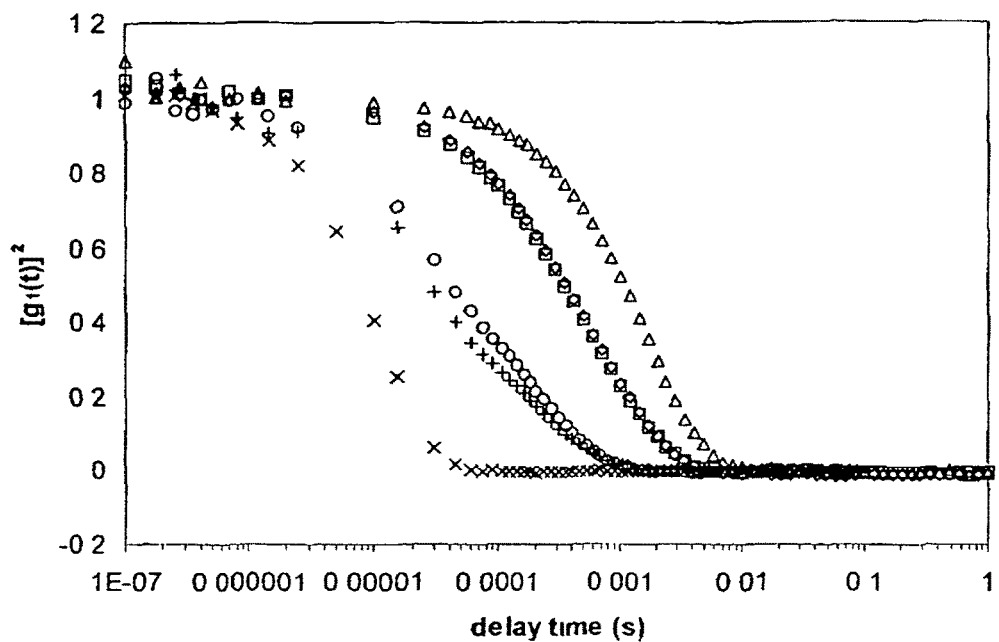
FIG. 5. Autocorrelation functions of 0.1% (w/w) EHEC, 0.1M $Li_2SO_4$, pH 2.5, and DTAB at an angle of 75° and temperature of 25° C. These functions include: no surfactant (◇), 1 mmolal DTAB (□), 5 mmolal DTAB (Δ), 160 mmolal DTAB (○), and 200 mmolal DTAB (+). The last function (x) includes 0.1M $Li_2SO_4$ and 200 mmolal DTAB but no polymer; thus, they represent DTAB micelles only. These micelles were determined to have a diameter of 4 nm based on center-of-mass diffusion of spheres.

The inventors characterized the interactions of DTAB and dilute EHEC via dynamic light scattering. FIG. 5 shows the ACFs of aqueous solutions (0.1M $Li_2SO_4$) containing dilute 0.1 wt % EHEC and various concentrations of DTAB. Inspection of FIG. 5 reveals that the ACF of EHEC in the presence of 1 mmolal DTAB is identical to the ACF of EHEC in solutions free of DTAB. The clouding temperature of EHEC solutions containing 1 mM DTAB is not measurably lowered as compared to solutions free of DTAB. At 5 mmolal DTAB, where the measurement is performed near the cloud point of 26-27° C., the ACF is shifted to longer delay times, revealing slower relaxation processes in these solutions as compared to solutions free of DTAB. The slow relaxation processes to indicate the presence of larger particles in the solution. This result is consistent with a model in which DTAB promotes aggregation of the polymer. This interpretation is consistent with cloud point measurements in FIG. 3, which reveal 5 mmolal DTAB to lower the clouding temperature of solutions of EHEC by 6° C. (from 32° C. to 26° C.). No light scattering measurements could be completed in solutions of EHEC containing 10 to 100 mmolal DTAB due to the clouding of these solutions at 25° C. At high DTAB concentrations, where solutions were optically transparent, the ACFs are shifted to shorter delay times as compared to the ACF of the solution of EHEC free of DTAB, indicating faster relaxation processes. This result appears to indicate that much smaller complexes are present in these solutions, consistent with a physical model in which EHEC aggregates have been dispersed by DTAB micelles. These results are qualitatively similar to past studies of the interactions between SDS and EHEC.

The ACF of EHEC in the presence of 200 mmolal DTAB shows slower relaxation processes than the ACF of 200 mmolal DTAB without EHEC. The CMC of DTAB in 0.1M $Li_2SO_4$ is 10 mM and the hydrodynamic diameter of DTAB micelles was determined to be 4 nm based on CM diffusion of spheres. The solution containing EHEC and 200 mmolal DTAB has an ACF that is different from the ACF of DTAB micelles. Therefore, the polymer-surfactant aggregate must be contributing to the ACF.

Figure 6:
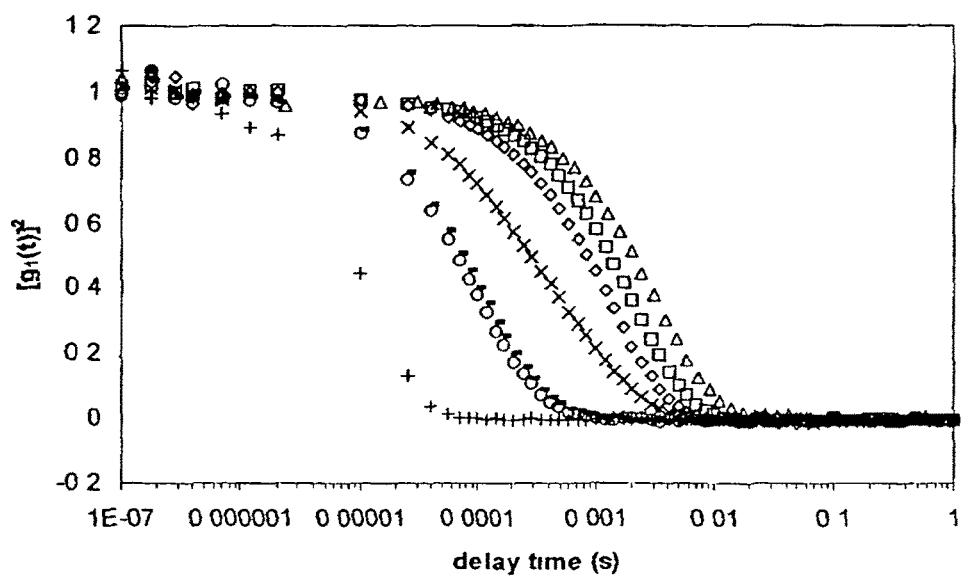
FIG. 6. Autocorrelation functions of 0.1% (w/w) EHEC, 0.1M $Li_2SO_4$, pH 2.5, and FTMA at an angle of 75° and temperature of 25° C. (a) Reduced FTMA: no surfactant (x), 0.1 mmolal (◇), 0.2 mmolal (□), 0.3 mmolal (Δ), 20 mmolal (−), and 25 mmolal (○). The last function (+) includes 0.1M $Li_2SO_4$ and 25 mmolal reduced FTMA but no polymer; thus, they represent micelles only. These micelles were determined to have a diameter of 6 nm based on center-of-mass diffusion of spheres. (b) Oxidized FTMA: no surfactant (x), 0.1 mmolal (◇), 0.2 mmolal (□), 0.3 mmolal (Δ), 1 mmolal (+), and 5 mmolal (○).
Figure 6:
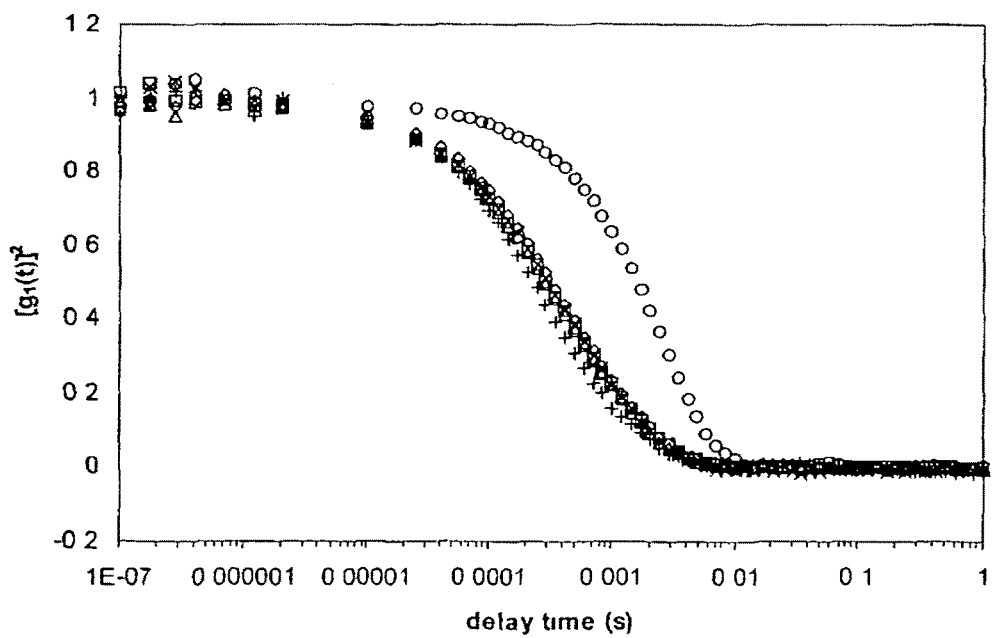

Next, dynamic light scattering measurements were performed on solutions containing EHEC and FTMA (FIG. 6). Similar to DTAB, the addition of 0.1 mmolal reduced FTMA to the aqueous solution of EHEC leads to a slowing of relaxation processes in the solution, consistent with a surfactant-promoted aggregation of EHEC. These processes become even slower as the concentration increases to 0.3 mmolal, above which solutions precipitated and were not measured by light scattering. The cloud point of 0.3 mmolal is ~25° C. At high concentrations of FTMA, the ACF reveals faster relaxation processes also similar to DTAB. The dynamic light scattering from these solutions is not dominated by FTMA micelles as the ACF obtained using a solution of EHEC with 25 mmolal FTMA differs from the ACF containing 25 mmolal FTMA only (no EHEC). The hydrodynamic diameter of reduced FTMA micelles (no polymer) was calculated to be 5 nm based on CM diffusion of spheres, which is consistent with previous studies.

FIG. 6b shows the ACFs for solutions of EHEC to which oxidized FTMA was added. From 0 to 1 mmolal oxidized FTMA, the ACF is unchanged from the ACF of EHEC free of surfactant. This indicates that these low concentrations of oxidized FTMA do not interact measurably with EHEC, unlike reduced FTMA, which promotes aggregation of EHEC at these same concentrations. This difference in aggregation is likely due to a difference in cooperativity. At a higher concentration of oxidized FTMA (5 mmolal), slower processes become evident in the ACF. This solution was measured at 25° C., which is close to its clouding temperature of 29° C. Above 5 mmolal oxidized FTMA, the solutions were cloudy and no light scattering measurements were performed. In contrast, surfactants that interact with EHEC cooperatively show dispersion of aggregates at higher concentrations.

Figure 7:
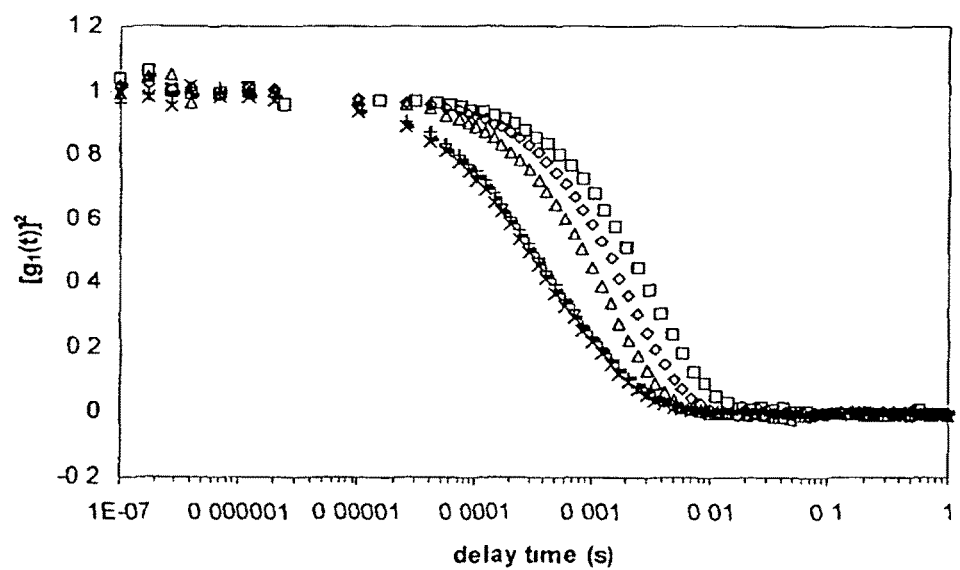
FIG. 7. Comparison of the autocorrelation functions of solutions containing oxidized and reduced FTMA at low concentrations of surfactant. All solutions contain 0.1% (w/w) EHEC, 0.1M $Li_2SO_4$, pH 2.5 and are measured at an angle of 75° and temperature of 25° C. The solutions include: 0.1 mmolal reduced FTMA (Δ), 0.1 mmolal oxidized FTMA (+), 0.2 mmolal reduced FTMA (◇), 0.2 mmolal oxidized FTMA (−), 0.3 mmolal reduced FTMA (□), and 0.3 mmolal oxidized FTMA (x). Reduced FTMA enhances aggregation of the EHEC aggregates, while oxidized FTMA has no measurable interaction with EHEC at these concentrations.

FIG. 7 compares the ACFs of solutions of EHEC containing the same concentrations of either oxidized or reduced FTMA. The ACFs show that solutions containing reduced FTMA have slower relaxation processes than the solutions containing oxidized FTMA. This result appears to indicate that solutions of reduced FTMA contain larger aggregates than solutions of oxidized FTMA solutions. This difference in behavior is apparently due to the cooperative nature of reduced FTMA, allowing it to interact with EHEC, which is lost when the surfactant is oxidized and hinders the interactions with EHEC. Based on the light scattering and cloud point results, the solution properties of dilute EHEC are modulated by the oxidation state and concentration of FTMA.

Both cloud point and dynamic light scattering demonstrate that control of the oxidation state of FTMA can be used to tune polymer-surfactant interactions in solutions of EHEC/FTMA/Li$_2$SO$_4$. Reduced FTMA is shown to behave similarly to other micelle-forming surfactants, changing the aggregation state of EHEC. At low concentrations, reduced FTMA enhances aggregation and at high concentrations, the aggregates are dispersed. Oxidized FTMA is not shown to interact strongly with dilute EHEC at low concentrations, but shows clouding behavior similar to a salt rather than a surfactant. Based on these results, redox-active surfactants appear useful in controlling the properties of polymer solutions.

Materials

DTAB was used as received (Aldrich, purity 99%). SDS was purchased from Aldrich and recrystallized three times from ethanol. FTMA was purchased from Dojindo Corporation (Gaithersburg, Md.) and was used without further purification. A sample of EHEC (DVT 96017) was provided by Akzo Nobel AB (Stenungsund, Sweden) and further purified according to methods outlined in the literature[3]. In brief, dilute (0.1 wt %) EHEC was dialyzed against Millipore water for 2 weeks then freeze-dried. The purified EHEC was dissolved in water at 0.2 wt % solution by stirring for 5-7 days around 5° C. Multiple samples were measured and determined to be similar on the basis of measurements of light scattering and cloud point.

Methods

Sample Preparation. Three samples of each solution were prepared to assess reproducibility. The following procedures were used to exclude oxygen from the solutions of reduced FTMA in order to prevent oxidation. The EHEC solution was filtered through 0.22 μm GV Millipore filter, placed under vacuum for 30-45 minutes, then bubbled with argon for another 30-45 minutes. This deaeration procedure was performed for all solutions, including solutions of DTAB.

The aqueous solutions of electrolyte used to prepare solutions of reduced FTMA (0.2M Li$_2$SO$_4$ at pH 2) underwent the same filtration and rigorous deaeration. The solutions of polymer, salt, and surfactant were then mixed to form 0.1 wt % EHEC, 0.1M Li$_2$SO$_4$, and the desired concentration of surfactant. These solutions were deaerated three times and bubbled with argon inside airtight containers. These solutions were stored at 25° C. and measured after 3 hours and 1 day. Due to oxidation (based on measurements of UV-Vis spectra), the autocorrelation functions for FTMA solutions changed slightly over the course of a few days. Very little change in light scattering characterization occurred over just 3 hours; therefore, the reduced FTMA-EHEC-Li$_2$SO$_4$ measurements performed after 3 hours were used for analysis. In contrast we characterized DTAB-EHEC-Li$_2$SO$_4$ solutions after 3 hours, 1 day, and 1 week and found no change in clouding temperature or autocorrelation functions over this interval of time.

The DTAB and oxidized FTMA solutions were not prepared with deaerated salt solution nor were the solutions deaerated after preparation. They were simply filtered, mixed to the desired concentrations, and stored for one day before measurements of cloud points and light scattering were performed.

Electrochemical Methods. FTMA was oxidized using a bipotentiostat (Pine Instruments, Grove City, Pa.) at 0.4V relative to a silver|silver chloride reference electrode. A three-electrode cell was used to maintain a constant 0.4V between the reference and working electrode. The working and counter electrodes were each one square inch platinum mesh. Full oxidation of FTMA was determined by measuring a UV-Vis spectrum and observing a constant current less that was than 0.05 mA at the end of the oxidation process.

Cloud Point Measurements. Solution of EHEC and surfactant were immersed in a temperature bath controlled to within 0.1° C. The temperature was increased by 1° C. every 10 minutes and the solutions were visually inspected for clouding. We also used longer equilibration times (30 minutes to 1 day per degree Celsius) and determined that the measured clouding temperature did not change with the rate of heating. The cloud point measured upon heating was higher than the cloud point measured upon cooling, as reported elsewhere[3,10,11]. The values reported in this study are based on clouding points measured upon increasing the temperature of the solutions.

Dynamic Light Scattering Measurements. A 100 mW, 532 nm laser (Coherent Compass 315M-100) illuminated a temperature-controlled glass cell at 25° C. filled with a refractive-index matching fluid (decahydronaphthalene). The scattering of light was measured at angles of 110, 90, 75, 60, and 45°. Delay times ranged from 50-100 ns to 1-10 s. The autocorrelation function was obtained by using a BI-9000AT digital autocorrelator (Brookhaven Instruments Corporation, Holtsville, N.Y.).

B. Interactions of FTMA and Hydrophobically-Modified ethyl(hydroxyethyl)cellulose (HM-EHEC)

Figure 8:
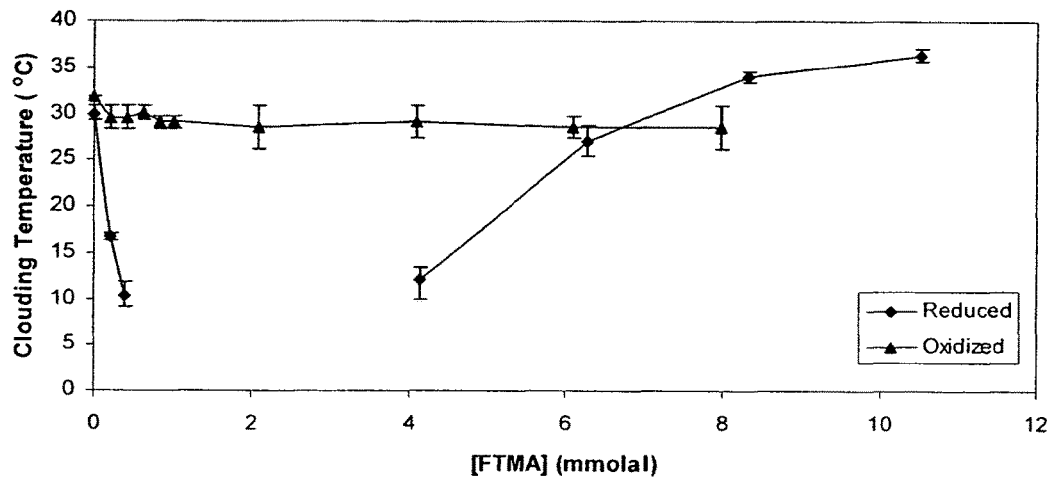
FIG. 8. A graph of clouding temperatures of 1% HM-EHEC, 0.1M Li2SO4, and FTMA.

The inventors have determined that it is possible to control the interactions of FTMA and hydrophobically modified polymers via measurements of the clouding temperature of 1 wt % hydrophobically-modified ethyl(hydroxyethyl)cellulose (HM-EHEC). The polymer was mixed with reduced and oxidized FTMA in the presence of 0.1M $Li_2SO_4$ (with initial pH of 2). Drastic differences in the clouding temperature of oxidized versus reduced FTMA mixed with HM-EHEC were observed. Reduced FTMA decreased the clouding temperature drastically at concentrations of 0.2 to 4 mmolal, with a minimum in the range of 1-4 mmolal. Clouding temperatures in this range were below our measurable temperature of 5° C. At higher concentrations of reduced FTMA (6-11 mmolal), the clouding temperature of HM-EHEC increased above the zero-surfactant clouding temperature. Oxidized FTMA, however, had very little effect on the clouding temperature of HM-EHEC. Referring to FIG. 8, the clouding temperature remained essentially constant over the entire concentration range tested (0.1-8 mmolal).

C. Interactions of Ferrocenylundecylsulfonate (FS) and HM-EHEC

FS is a ferrocenyl surfactant that possesses an anionic head group. The inventors have performed experiments that demonstrate that it is possible to control the interactions of 11-ferrocenylundecylsulfonate (FS) and HM-EHEC in the presence of 10 mM $Li_2SO_4$ at pH of 5. These experiments demonstrated that reduced FS caused a liquid-liquid phase separation in the presence of HM-EHEC. For example, 1 mmolal reduced FS, 1 wt % HM-EHEC, and 10 mM $Li_2SO_4$ was observed to separate into 2 liquid layers. The top layer had low viscosity (similar to that of water) and was mildly cloudy; the bottom layer was yellow and highly viscous, almost gel-like. As the concentration of reduced FS increased, the top layer became more cloudy and the bottom layer became less viscous (up to 5 mmolal). As the concentration of reduced FS was decreased (down to 0.1 mmolal), the top layer cleared and the bottom layer became less viscous. In contrast, oxidized FS did not form two coexisting liquid phases. The solutions made with oxidized FS were faintly blue and cloudy as the concentration increased (from 0.1 to 0.5 mmolal).

D. Use of Glutathione to Reduce Oxidized FTMA

An oxidized solution of FTMA was prepared in 1 mM $Li_2SO_4$ at pH 5. The inventors then added various concentrations of glutathione (GHS) and measured the UV-Vis spectrum of the samples after a few hours. The final concentration of FTMA was 0.5 mM and GHS was 1-50 mM. It was determined that 1 mM GHS reduced ~4% of the FTMA and 50 mM GHS reduced 97% of the FTMA (as shown in Table 1 below). This experiment demonstrates that reducing and oxidizing agents found in biological systems can change the oxidation states of redox-active surfactants, as contemplated herein.

TABLE 1

| [GHS] (mM) | Percent of FTMA reduced |
|---|---|
| 1 | 4 |
| 5 | 42 |
| 10 | 79 |
| 50 | 97 |

E. Interactions of BSA and FTMA

All solutions were prepared using filtered and deaerated solutions of 0.1M $Li_2SO_4$ at pH 6. Bovine serum albumin and FTMA solutions were mixed to final concentrations of 0.15M and 10-500 µM, respectively. An oxidized solution of 1 mM FTMA was prepared electrochemically by applying an external potential of 0.4V for approximately 1 hour. The solution was determined to be oxidized by visual inspection and UV-Visible spectroscopy.

Figure 9:
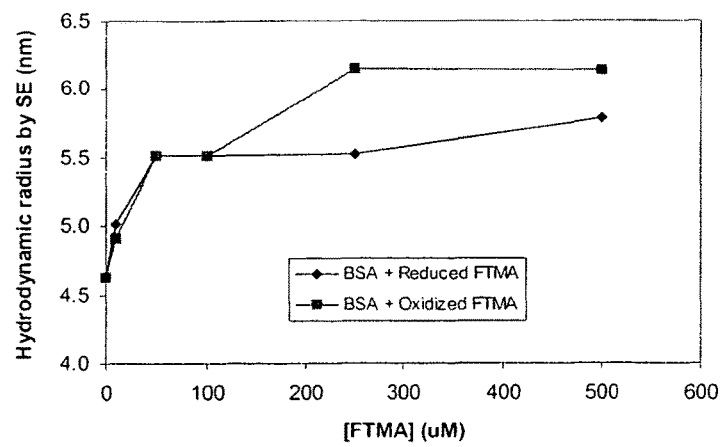
FIG. 9. A graph displaying sizes of BSA and FTMA aggregates.

Measurements of dynamic light scattering were performed on all solutions at a scattering angle of 90° and a temperature of 25° C. Samples were measured 30-60 minutes after preparation. The autocorrelation functions were interpreted using a single exponential function to yield a hydrodynamic size of the BSA+FTMA aggregates in solution. Inspection of FIG. 9 reveals that the hydrodynamic size of BSA in the presence of oxidized FTMA is different from the hydrodynamic size of BSA in the presence of reduced FTMA. This result demonstrates that the oxidation state of the FTMA can be used to tune the interaction between the ferrocenyl surfactant and the protein BSA.

F. Interactions of DNA and FTMA

All solutions were prepared using filtered and deaerated solutions of 1 mM $Li_2SO_4$ at pH 5. Salmon sperm DNA and FTMA solutions were mixed to final concentrations of 200 µM DNA (in nucleotide units) and 10-500 µM FTMA. An oxidized solution of 1 mM FTMA was prepared electrochemically by applying an external potential of 0.4V for approximately 3 hours.

Measurements of dynamic light scattering were performed on all solutions at scattering angles of 110, 90, 75, and 60° and a temperature of 25° C. Samples were measured 30-120 minutes after preparation.

Figure 10:
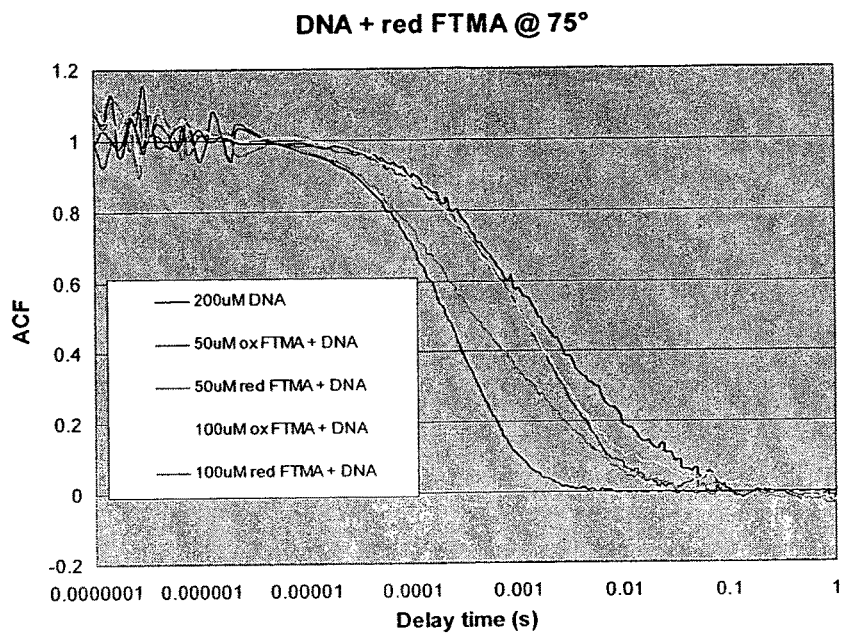
FIG. 10. A graph of autocorrelation function versus delay time for DNA+reduced FTMA at 75° C.

Inspection of the autocorrelation functions obtained from dynamic light scattering measurements at an angle of 75° at 50 µM FTMA (FIG. 10), reveal that the oxidation state of FTMA changes the interaction of the DNA and FTMA.

Figure 11:
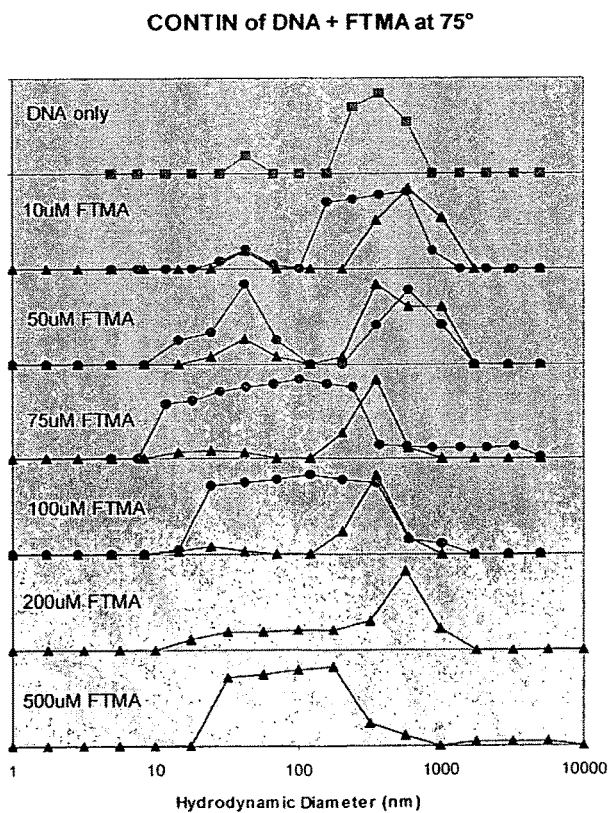
FIG. 11. Plots of CONTIN data for DNA plus FTMA at 75° C.

The data shown in FIG. 11 and Table 2 show the size distributions of DNA+FTMA complexes, measured at a scattering angle of 75°, for the indicated concentrations of oxidized and reduced FTMA. These results also demonstrate that the interactions of DNA and FTMA depend on the oxidation state of the FTMA.

In addition to the light scattering results below, solutions containing 200 and 500 µM reduced FTMA created precipitates with DNA. In contrast, oxidized FTMA+DNA did not precipitate.

TABLE 2

|  | Reduced FTMA | | Oxidized FTMA | |
| --- | --- | --- | --- | --- |
| [FTMA] (μM) | Peak 1 Diameter (nm) | Peak 2 Diameter (nm) | Peak 1 Diameter (nm) | Peak 2 Diameter (nm) |
| 0 | 52 | 497 | 52 | 497 |
| 10 | 45 | 372 | 40 | 504 |
| 50 | 35 | 490 | 48 | 410 |
| 75 | 97 |  | 37 | 440 |
| 100 | 142 |  | 56 | 384 |
| 200 |  |  | 70 | 557 |
| 500 |  |  | 143 |  |

G. Light Scattering Measurements Demonstrating BFDMA-DNA Interactions can be Manipulated by Control of the Oxidation State of BFDMA.

The inventors prepared aqueous solutions of DNA and BFDMA using the methods described below, and measured the hydrodynamic size of the aggregates present in these solutions as a function of the oxidation state of the BFDMA. Inspection of Table 3 reveals that the sizes of aggregates formed by DNA in the presence of reduced BFDMA are much larger than the sizes of aggregates present when BFDMA is oxidized. These results demonstrate that the interactions of DNA and BFDMA can be changed via changes in the oxidation state of the BFDMA.

TABLE 3

| time (min) | red w/o DNA (nm) | red w/ DNA (nm) | ox w/o DNA (nm) | ox w/ DNA (nm) |
| --- | --- | --- | --- | --- |
| 0 | 472.8 | 689.7 | 363.4 | 209.6 |
| 120 | 1214 | 2613.9 | 496 | 221.4 |
| 240 | 1090.3 | 2995.5 | 511 | 297.2 |

Preparation of BFDMA Stock Solutions

1) A solution of 100 μM reduced BFDMA was prepared by dissolving BFDMA (solid) in water.

2) A solution of 100 μM oxidized BFDMA was prepared as follows: First, a 1 μM reduced BFDMA solution was prepared by dissolving BFDMA (solid) in 1 mM $Li_2SO_4$ aqueous solution, and then the solution was oxidized electrochemically. The resultant oxidized BFDMA solution was diluted with water to give a solution of 100 μM oxidized BFDMA.

Sample Preparation of BFDMA Solutions without DNA.
150 μl of 100 μM reduced/oxidized BFDMA solution was diluted with 150 μl of water, followed by the addition of 1.2 ml of Opti-MEM. The final BFDMA concentration was 10 μM. QLS measurements were made at 25° C. immediately after the samples were prepared.

Sample Preparation of BFDMA Solutions with DNA (BFDMA/DNA Complexes)

1) 150 μl of 100 μM reduced/oxidized BFDMA solution was diluted with 150 μl of 24 μg/ml pGFP aqueous solution, and the solution was allowed to stand for 20 min at room temperature. 1.2 ml of Opti-MEM was added to the solution to yield a final BFDMA concentration of 10 μM and a final DNA concentration of 2.4 μg/ml. QLS measurements were made at 25° C. immediately after the samples were prepared.

Example 2

Delivery of Plasmid DNA to Cells Using bis-(11-ferrocenylundecyl)dimethylammonium bromide (BFDMA)

A. Materials and Methods

Materials. Dulbecco's Modified Eagle's Medium (DMEM), OptiMEM cell culture medium, phosphate buffered saline, and fetal bovine serum (FBS) were purchased from Invitrogen (Carlsbad, Calif.). Bis-(11-ferrocenylundecyl)dimethylammonium bromide (BFDMA) was synthesized as previously described (Kakizawa, et al., Langmuir 1996, 12, 921-924; Kakizawa, et al., *Langmuir* 2001, 17, 8044-8048). BFDMA was determined to be >95% pure by $^1$H NMR spectroscopy and no impurities were observed upon analysis by electrospray ionization (ESI) mass spectrometry. Plasmid DNA encoding enhanced green fluorescent protein [pEGFP-N1 (4.7 kb), >95% supercoiled] was obtained from the Waisman Clinical Biomanufacturing Facility at the University of Wisconsin—Madison. Plasmid DNA encoding firefly luciferase [pCMV-Luc, >95% supercoiled] was obtained from a commercial supplier (Elim Biopharmaceuticals, Inc., San Francisco, Calif.). Deionized water (18 MΩ) was used to prepare all buffers and salt solutions. Lipofectamine 2000 was purchased from Invitrogen (Carlsbad, Calif.) and TransIT-LT1 was purchased from Mirus Bio Corporation (Madison, Wis.). Live/dead viability/cytotoxicity assay kits were purchased from Molecular Probes (Carlsbad, Calif.) and BCA protein assay kits were purchased from Pierce (Rockford, Ill.). Glo Lysis Buffer and Steady-Glo Luciferase Assay Systems were purchased from Promega Corporation (Madison, Wis.). All commercial materials were used as received without further purification unless otherwise noted.

General Considerations. Oxidation of BFDMA was conducted at 70° C. using a bipotentiostat (Pine Instruments, Grove City, Pa.) and a three-electrode cell to maintain a constant potential of 500 mV between the working electrode and a Ag/AgCl reference electrode, as described previously Abbott, et al., *J Am Chem Soc* 2005, 127, 11576-7. Platinum mesh (1.0 $in^2$) was used as the working and counter electrodes. The progress of oxidation was followed by monitoring current passed at the working electrode and by UV/visible spectrophotometry. UV/visible absorbance values were recorded on a Beckman Coulter DU520 UV/vis Spectrophotometer (Fullerton, Calif.). Dynamic light scattering experiments were conducted using a 100 mW 532 nm laser (Coherent Compass 315M-100) illuminating a temperature-controlled glass cell (maintained at 37° C.) filled with a refractive-index matching fluid (decahydronaphthalene). Autocorrelation functions were obtained using a BI-9000AT digital autocorrelator (Brookhaven Instruments Corporation, Holtsville, N.Y.). Fluorescence microscopy images used to evaluate the expression of enhanced green fluorescent protein in transfection experiments were recorded using an Olympus IX70 microscope and were analyzed using the Metavue version 4.6 software package (Universal Imaging Corporation). Fluorescent image acquisition settings were identical for all samples, using an exposure time of 400 ms, a gain of +0.25, and a binning of 2. Data were stored in single channel, 12-bit TIF format. Additional image processing was limited to false coloring and scaling. Fluorescence, luminescence, and absorbance measurements used to characterize cytotoxicity, luciferase expression, and total cell protein were made using a PerkinElmer EnVision multilabel plate reader (Live: Ex: 492 nm, Em: 535 nm; Dead: Ex: 535 nm, Em: 620 nm; Luciferase: Em: 700 nm cutoff; BCA: Ex: 560 nm).

Preparation of Reduced and Oxidized BFDMA Solutions. Solutions of reduced BFDMA were prepared by dissolving a desired mass of purified reduced BFDMA in aqueous $Li_2SO_4$ (1.0 mM) followed by serial dilution with water over the desired concentration range. Solutions of oxidized BFDMA were prepared by electrochemical oxidation of a 1.0 mM $Li_2SO_4$ solution containing reduced BFDMA, followed by serial dilution to desired concentrations.

Preparation of lipoplexes for Transfection Assays. DNA lipoplexes prepared from oxidized and reduced BFDMA were prepared in the following general manner. A solution of plasmid DNA (600 ng in 25 μL of water) was added to a vortexing solution of aqueous $Li_2SO_4$ (25 μL) containing reduced or oxidized BFDMA to produce a 5× stock formulation. The amount of BFDMA used to prepare each stock formulation was selected such that a five-fold dilution of this stock into 200 μL of cell culture medium yielded the final lipid concentrations reported in the text (e.g., Table 1). Samples were allowed to stand at room temperature for a minimum of ten minutes (typically 30 minutes). Control samples were prepared using 600 ng of plasmid and either Lipofectamine 2000 (Invitrogen) or TransIT-LT1 (Mirus-Bio) according to the manufacturers' recommended protocols.

General Protocols for Transfection and Analysis of Gene Expression. COS-7 cells used in transfection experiments were grown in clear or opaque polystyrene 96-well culture plates (for experiments using pEGFP-N1 and pCMV-Luc, respectively) at initial seeding densities of 15,000 cells/well in 200 μL of growth medium (90% Dulbecco's modified Eagle's medium, 10% fetal bovine serum, penicillin 100 units/mL, streptomycin 100 μg/mL). After plating, all cells were incubated at 37° C. for 24 hours and transfection experiments were conducted at approximately 80% confluence. These experiments were performed in parallel in serum-containing medium (DMEM+10% FBS) and serum free medium (OptiMEM). Immediately prior to the addition of lipoplexes (as discussed below), culture medium was aspirated from each well and replaced with 200 μL of DMEM (for transfections conducted in the presence of serum) or 200 μL of OptiMEM (for transfections conducted in the absence of serum).

For experiments conducted using pEGFP-N1, formulations of lipoplexes (50 μL) prepared at desired pEGFP-N1: BFDMA ratios were added to assigned wells via pipette, and the cells were incubated for four hours at 37° C., at which point lipoplex-containing media was aspirated from all wells and replaced with 200 μL of serum-containing medium. Cells were then incubated for 48 hours and cell morphology and relative levels of EGFP expression were characterized using phase contrast and fluorescence microscopy.

For experiments conducted using pCMV-Luc, formulations of lipoplexes (50 μL) prepared at desired pCMV-Luc: BFDMA ratios were added to assigned wells via pipette, and the cells were incubated for two, four, or twelve hours at 37° C. After these incubation periods, lipoplex-containing culture medium was aspirated from all wells and replaced with 200 μL of fresh serum-containing medium. Cells were then incubated for 48 hours. Quantitative cytotoxicity measurements were conducted in replicates of six using a commercially available fluorescence live/dead assay kit (Molecular Probes) according to the manufacturer's protocol. Luciferase protein expression was determined using a commercially available luminescence-based luciferase assay kit (Promega) using the manufacturer's specified protocol. Samples, in replicates of six, were compared with signals from control wells and/or normalized against total cell protein in each respective well using a commercially available bicinchoninic acid (BCA) assay kit (Pierce).

Dynamic Light Scattering Experiments and Analysis of Autocorrelation Functions. Water and aqueous $Li_2SO_4$ solutions used for light scattering were filtered through a series of two 0.22 μm GV Millipore syringe filters and degassed with argon for 30 minutes prior to adding lipid or DNA. Lipoplexes were prepared as described above at final concentrations of BFDMA (2 μM, 6 μM, 8 μM, 10 μM, etc.) and pEGFP-N1 (2.4 μg/ml) representative of those used in the transfection experiments described above. The scattering of light was measured at angles of 110°, 90°, 75°, 60°, 45° and 30° with delay times ranging from 100 ns to 1-10 s. Autocorrelation functions (ACF) for the intensity of the scattered light were analyzed using the CONTIN software package S. W. Provencher, A Constrained Regularization Method for Inverting Data Represented by Linear Algebraic or Integral Equations. *Computer Physics Communications* 1982, 27, 213-227; S. W. Provencher, CONTIN: A General Purpose Constrained Regularization Program for Inverting Noisy Linear Algebraic and Integral Equations. *Computer Physics Communications* 1982, 27, 229-242. to yield a distribution of aggregate sizes by assuming that the relaxation processes in solution correspond to center-of-mass diffusion.

B. Initial Studies and Electrochemical Characterization of BFDMA

Subsequent studies described below were focused on investigating the behavior of the two-tailed cationic lipid bis(11-ferrocenylundecyl)dimethylammonium bromide (BFDMA, FIG. 1) recently reported by Abe and coworkers (Kakizawa, et al., *Langmuir* 1996, 12, 921-924; Kakizawa, et al., *Langmuir* 2001, 17, 8044-8048). The two-tailed structure of BFDMA is similar to the cationic lipid dimethyldioctadecylammonium bromide (DDAB). Ferrocene and ferrocene derivatives have been investigated in numerous biotechnological contexts owing to the stability of the bis (cyclopentadienyl) iron structure in physiological media and the low electrochemical potentials required to oxidize and reduce ferrocene derivatives (ranging from 0 mV to 500 mV, vs. a Ag/AgCl electrode). In addition, a rapidly growing body of literature describes the evaluation of ferrocene-containing therapeutics in several physiological contexts. For all experiments described below, oxidized BFDMA was synthesized by bulk electrolysis of reduced DNA, and all lipid solutions were prepared and characterized as described previously by Abbott, et al. (*J Am Chem Soc* 2005, 127, 11576-7).

C. Preparation of Lipoplexes and Qualitative Transfection Experiments

Lipoplexes were prepared using plasmid DNA and solutions of either reduced or oxidized BFDMA in concentrations sufficient to give a broad range of final lipid concentrations (ranging from 2 μM to 60 μM) when these formulations were diluted into 200 μL of cell culture medium (see Materials and Methods Section for complete details). The full range of final lipid concentrations used in this investigation is shown in Table 4.

TABLE 4

Molar concentrations of BFDMA used to prepare lipoplexes for transfection experiments and corresponding lipid:DNA charge/charge ratios.

| Concentration of BFDMA (µM)[a] | Charge Ratio (BFDMA$_{Red}$:DNA)[b] | Charge Ratio (BFDMA$_{Ox}$:DNA)[b] |
| --- | --- | --- |
| 2 | 0.3 | 0.8 |
| 4 | 0.6 | 1.7 |
| 6 | 0.8 | 2.5 |
| 8 | 1.1 | 3.3 |
| 10 | 1.4 | 4.1 |
| 20 | 2.8 | 8.3 |
| 40 | 5.5 | 16.5 |
| 60 | 8.3 | 24.8 |

[a]Concentration shown represents the molar concentration of BFDMA upon dilution of lipoplex formulations into 200 µL of cell culture medium, as described in the text and experimental section.
[b]Charge/charge ratios are based on charge resulting from ammonium functionality and presence or absence of ferrocenium ion (for BFDMA) and phosphate functionality (for DNA). All calculations are based on the formation of lipoplexes using 600 ng of DNA.

With regard to the nomenclature used to describe lipoplex formulations in all transfection and characterization experiments discussed below, each formulation is described using the final molar concentration of lipid used to prepare the lipoplexes rather than the lipid/DNA charge/charge ratios used conventionally to describe lipoplex formulations. The current study aims to characterize the behavior of lipoplexes formed from either reduced BFDMA or oxidized BFDMA, both of which have discrete charge densities (see structures in FIG. 1). However, future studies could involve the in situ reduction or oxidation of previously prepared lipoplex formulations (during which the charge density of the lipids in the formulation would vary, but the molar concentration of lipid would remain constant). In the context of evaluating the behavior of reduced and oxidized BFDMA and also establishing a basic framework from which to pursue these more advanced studies, the toxicity and transfection activity of these materials are described and compared at equivalent molar concentrations in this study (Table 4). However, for reference, and to facilitate the comparison of the results of this study to those reported using other lipids, Table 4 shows charge/charge ratios calculated for lipoplexes prepared from both reduced and oxidized BFDMA at each molar concentration of lipid used in this investigation.

Figure 12:
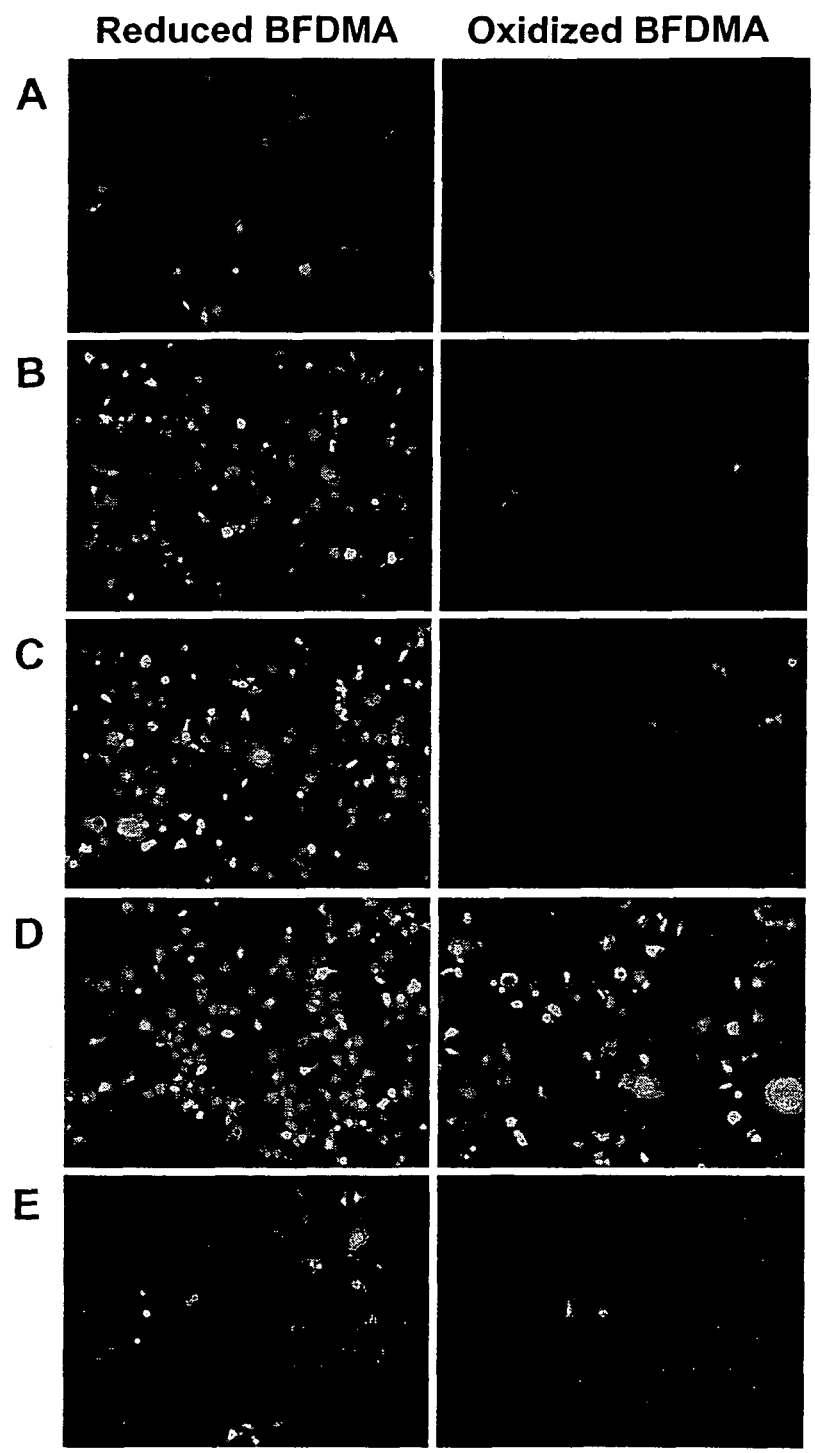
FIG. 12. Expression of EGFP in COS-7 cells treated with lipoplexes of pEGFP-N1 and either reduced or oxidized BFDMA. Images were collected 48 hours after exposure of cells to lipoplexes in serum-free medium. Concentrations of reduced BFDMA (left) and oxidized BFDMA (right) are: A) 2 μM, B) 6 μM, C) 10 μM, D) 20 μM, and E) 40 μM.

To determine the ability of BFDMA to transfect cells, a series of qualitative gene expression assays was performed in the COS-7 cell line using lipoplexes prepared from a plasmid DNA construct (PEGFP-N1) encoding enhanced green fluorescent protein (EGFP). FIG. 12 shows fluorescence microscopy images collected 48 hours after the exposure of lipoplexes to cells (the results of five representative concentrations are shown). For these experiments, cells were incubated with lipoplexes for four hours in serum-free medium, followed by incubation in fresh serum-containing medium (see Materials and Methods Section for complete description of transfection procedures). These results are consistent with the results of a previous investigation Abbott, et al. (*J Am Chem Soc* 2005, 127, 11576-7, incorporated herein by reference) and demonstrate qualitatively that while BFDMA is capable of mediating the transfection of cells, the extent of transfection depends significantly upon both the concentration of BFDMA and the oxidation state of the lipid used to prepare the lipoplexes. As shown in FIG. 12, lipoplexes prepared using low concentrations of reduced BFDMA (e.g., 2 µM) yielded relatively low levels of EGFP expression. Transfection increased significantly at higher concentrations (e.g., 10 µM and 20 µM) and was significantly reduced at a concentration of 40 µM. Significant cell death was observed at concentrations of reduced BFDMA above 40 µM, as determined visually by phase contrast microscopy.

The experiments above demonstrate qualitatively that reduced BFDMA is capable of mediating high levels of gene expression over a broad range of lipid concentrations. By contrast, experiments using oxidized BFDMA generally resulted in very low levels of gene expression (FIG. 12, right column) typical of control experiments using DNA in the absence of lipid. Inspection of these data, however, reveals relatively high levels of cell transfection in experiments using lipoplexes prepared at a concentration of 20 µM oxidized BFDMA. The reasons for the increase in transfection at this specific lipid concentration are not yet completely understood. However, this result was observed in multiple different repetitions of this experiment as well as in quantitative transfection experiments using a plasmid encoding firefly luciferase, and may result from an increase in the sizes of the lipoplexes formed at this concentration (as described below). Taken collectively, the EGFP expression data in FIG. 12 demonstrate qualitatively that a window of concentration exists over which reduced BFDMA yields high levels of transfection, but oxidized BFDMA does not.

D. Quantitative Characterization of Gene Expression and Cytotoxicity

To characterize quantitatively the large differences in gene expression observed in FIG. 12 and benchmark the transfection efficiency and cytotoxicity of BFDMA against commercial cationic lipid reagents, a second set of transfection experiments was conducted using lipoplexes prepared from a plasmid DNA construct (pCMV-Luc) encoding firefly luciferase. For these experiments, lipoplexes were incubated with cells for two, four, or twelve hours in serum-free culture medium, after which medium was replaced with fresh serum-containing growth medium. Forty-eight hours after cells were first exposed to lipoplexes, cytotoxicity was characterized quantitatively using a commercially available calcein/ethidium homodimer live/dead fluorescence assay and levels of gene expression were determined quantitatively using a luminescence-based protocol.

Cytotoxicity. FIG. 13 shows the results of quantitative cytotoxicity assays for cells treated with lipoplexes prepared using concentrations of reduced and oxidized BFDMA ranging from 2 µM to 60 µM. These data represent the percentage of dead cells observed (relative to a cell control consisting of untreated cells killed by exposure to methanol) after incubation with lipoplexes for two, four, and twelve hours; control experiments using naked DNA (no lipid) and two commercially available cationic lipid reagents (Lipofectamine 2000 and TransIT-LT1) are provided for comparison. Inspection of the data in FIG. 13a, which correspond to an incubation/exposure time of two hours, demonstrates that lipoplexes prepared from oxidized BFDMA are not cytotoxic relative to DNA alone or commercial controls at any concentrations evaluated. These data also demonstrate that reduced BFDMA is not cytotoxic at concentrations ranging from 2 µM to 10 µM. The cytotoxicity of reduced BFDMA increases slightly at a concentration of 20 µM and reduced BFDMA is substantially cytotoxic at concentrations of 40 µM and 60 µM. FIGS. 13b and 13c correspond to experiments for which cells were exposed to lipoplexes for four and twelve hours, respectively. The cytotoxicity profile after exposure to lipoplexes for four hours is similar to the profile measured after exposure for two hours, although the toxicity of lipoplexes formed from oxidized lipid increases at higher concentrations (e.g. 40 µM and 60 µM). For 12-hour exposure times, the toxicity of reduced and oxidized BFDMA increases at higher concentrations of lipid. For example, whereas lipoplexes prepared using reduced BFDMA at 20 µM are not substantially cytotoxic upon exposure for two or four hours (FIGS. 13a and 13b), this concentration of reduced lipid is cytotoxic when exposed to cells for 12 hours (FIG. 13c). Further, lower concentrations of reduced BFDMA (e.g., from 6 µM to 10 µM) that are not cytotoxic upon exposure for two or four hours were measured to be more cytotoxic upon exposure for 12 hours (FIG. 13c).

E. Luciferase Expression Assays.

FIGS. 14a-c show quantitative luciferase gene expression data (normalized to total cell protein) using lipoplexes prepared from reduced and oxidized BFDMA at concentrations and conditions identical to those used to characterize cytotoxicity in FIGS. 13a-c. The results shown in FIG. 14a correspond to a lipoplex exposure time of two hours and are in general agreement with the results of the EGFP expression data in FIG. 12. These results demonstrate quantitatively that the extent of transfection is dependent upon both the concentration of BFDMA and the oxidation state of the lipid. For experiments performed using reduced BFDMA, luciferase expression is low at both low concentrations (e.g. 2 µM) and high concentrations (40 µM and 60 µM) of lipid. At intermediate concentrations of reduced BFDMA (e.g., 4 µM to 20 µM), luciferase expression was significantly higher. In contrast to the results obtained using reduced BFDMA, quantitative levels of gene expression measured using oxidized BFDMA were dramatically lower and, in general, representative of levels typical of naked DNA (no lipid) control experiments (FIG. 14a). Gene expression using oxidized BFDMA reached a maximum value at 20 µM, although the magnitude of expression remained significantly lower than the magnitude of expression resulting from the use of 20 µM reduced BFDMA. This result is consistent with the qualitative EGFP expression results shown in FIG. 12, for which a maximum in expression was also observed using 20 µM oxidized BFDMA.

FIGS. 14b and 14c show luciferase transfection data resulting from the incubation of cells with lipoplexes for fours hours and twelve hours in serum-free medium. Levels of luciferase expression using reduced BFDMA were higher at these longer exposure times and were, at concentrations ranging from 6 µM to 20 µM, either comparable to or measured to be in excess of the levels of gene expression measured using Lipofectamine 2000 and TransIT-LT1, two commercially available and widely used cationic lipid-based transfection agents. With respect to differences in expression using reduced and oxidized BFDMA, the transfection results at these longer exposure times are similar to those shown in FIG. 14a. However, several additional points deserve comment. First, the levels of gene expression mediated by oxidized BFDMA increase significantly at longer exposure times (relative to the levels observed after two hours of incubation in FIG. 14a). As a result, the relative differences between the levels of gene expression using reduced and oxidized lipid change significantly in several cases (e.g., at 20 µM concentrations of lipid). This difference is particularly notable for 12 hour exposure times (FIG. 14c), for which expression mediated by lipoplexes formed from oxidized BFDMA at 20 µM was measured to be in excess of expression mediated by reduced BFDMA. It is possible that the increases in expression observed using oxidized lipid could result from more extensive internalization of lipoplexes at these longer incubation times. For example, measurements of lipoplex sizes using dynamic light scattering demonstrate that lipolexes formulated at 20 µM oxidized BFDMA are considerably larger than lipoplexes formulated at lower lipid concentrations (as discussed below). It is possible, therefore, that these larger complexes could sediment more efficiently onto cells during this extended 12 hour incubation period. Because both absolute levels of transgene expression and cytotoxicity may be important from the standpoint of eventual applications of these materials, the results above suggest that concentrations of reduced BFDMA ranging from 6 µM to 10 µM may be most useful under these conditions.

FIG. 15 shows normalized luciferase expression resulting from the incubation of lipoplexes with cells for four hours in cell culture medium supplemented with 10% fetal bovine serum. These data are qualitatively similar to the results of experiments shown in FIG. 14b, for which cells were incubated with lipoplexes in serum-free medium, in that large differences in transfection are observed for reduced and oxidized lipid. However, further inspection reveals that the concentrations at which maximum gene expression is observed are shifted higher relative to transfection in serum-free medium (e.g., 20 µM and 40 µM for reduced BFDMA and 40 µM and 60 µM for oxidized BFDMA), and that the large differences between the activity of reduced and oxidized BFDMA are maintained up to concentrations of 40 µM in the presence of serum. Further, it is noted the magnitudes of gene expression observed in the presence of serum were measured to be approximately one order of magnitude lower relative to transfection in serum-free medium. These results are in agreement with the qualitative observations reported above for the expression of EGFP in serum-free and serum-containing media. Taken collectively, the transfection data in FIGS. 12, 14 and 15 reveal that differences in the oxidation state of BFDMA yield large differences in cell transfection. In combination with the cytotoxicity data in FIG. 13, these data demonstrate that a broad range of concentration exists over which reduced BFDMA is non-cytotoxic and mediates high levels of transfection, but oxidized BFDMA is non-cytotoxic and does not mediate high levels of transfection.

F. Dynamic Light Scattering and Characterization of Aggregate Sizes

One important physical parameter that influences the ability of lipids to mediate cell transfection efficiently is the size of the condensed lipid/DNA aggregates that are formed. Although many additional factors contribute to the overall efficiency of transfection, aggregate size affects the degree to which particles are internalized by endocytosis as well as the rates at which complexes may sediment onto cells during in vitro transfection experiments. For potential applications in vivo, the sizes of lipid/DNA aggregates may also place constraints on the routes through which different lipid formulations can be administered. Abe and coworkers reported recently that BFDMA forms micrometer-scale aggregates in the reduced state, and that the oxidation of reduced BFDMA solutions yields smaller aggregates. Thus, the structure and redox-behavior of BFDMA provide a mechanism for control over the charge density of the lipid and a mechanism for control over the interactions of the lipid with itself or other agents in aqueous solution.

Dynamic light scattering was used to characterize the sizes of lipoplexes formed using reduced and oxidized BFDMA. Lipoplexes were prepared and diluted into serum-free cell culture medium to yield final concentrations of BFDMA and pEGFP-N1 identical to those used in the transfection and cytotoxicity experiments described above. Table 5 shows the number-weighted and intensity-weighted average particle diameters measured for each lipoplex formulation.

TABLE 5

Number-averaged and intensity-averaged diameters for BFDMA/DNA lipoplexes determined by dynamic light scattering.[a]

| [BFDMA] ($\mu$M)[a] | Red. BFDMA Number-Avg Diameter (nm) | Ox. BFDMA Number-Avg Diameter (nm) | Red. BFDMA Intensity-Avg Diameter (nm) | Ox. BFDMA Intensity-Avg Diameter (nm) |
|---|---|---|---|---|
| 2 | 158 (±64) | 89 (±40) | 369 (±74) | 196 (±86) |
| 6 | 231 (±88) | 64 (±25) | 603 (±262) | 217 (±58) |
| 8 | 297 (±126) | 86 (±37) | 951 (±504) | 228 (±100) |
| 10 | 219 (±126) | 110 (±55) | 1118 (±426) | 266 (±212) |
| 20 | 1490 (±750) | 611 (±183) | 2766 (±725) | 1163 (±150) |
| 60 | 1921 (±1220) | 1254 (±512) | 4777 (±1350) | 1497 (±340) |

[a]Diameters measured in serum-free cell culture medium using lipid and DNA concentrations identical to those used in transfection and cytotoxicity experiments (see also Table 4). See experimental section for details related to data processing and calculation of average particle sizes and size distributions. All experiments were conducted using lipoplexes formulated using 600 ng of DNA.

As described in the Materials and Methods Section, all calculations of sizes were made based on the assumption that relaxation times resulting from analysis of the autocorrelation functions corresponded to center-of-mass diffusion of the aggregates in solution.

Inspection of the number-averaged values for lipoplexes formed using reduced BFDMA reveals aggregate sizes ranging from ca. 150 to 270 nm at lipid concentrations ranging from 2 $\mu$M to 10 $\mu$M, and that aggregate sizes increase considerably (e.g., from ca. 1.5 $\mu$m to 2.0 $\mu$m) at concentrations of 20 $\mu$M and 60 $\mu$M reduced BFDMA. DNA complexes with diameters of about 250 nm or less fall within the range of sizes generally considered suitable for efficient internalization by endocytosis E. Wagner, M. Ogris, W. Zauner, Polylysine-based transfection systems utilizing receptor-mediated delivery *Adv Drug Deliv Rev* 1998, 30, 97-113. In general, the sizes shown in Table 5 correlate well to the concentrations at which the highest levels of transfection are observed using lipoplexes prepared using reduced BFDMA (FIG. 14). Further, it is noted that reductions in transfection efficiency were observed to begin at higher concentrations of lipid (e.g., 20 $\mu$M and above) that lead to the formation of larger, micron-sized aggregates that may be internalized less efficiently by cells. It is not possible to discount on the basis of this current study the possibility that these larger aggregates may also contribute to the increased cytotoxicity observed at these higher lipid concentrations. The cytotoxicity of lipoplexes formulated using oxidized BFDMA was also observed to increase at concentrations of lipid that lead to the formation of large aggregates (as discussed below).

Figure 4:
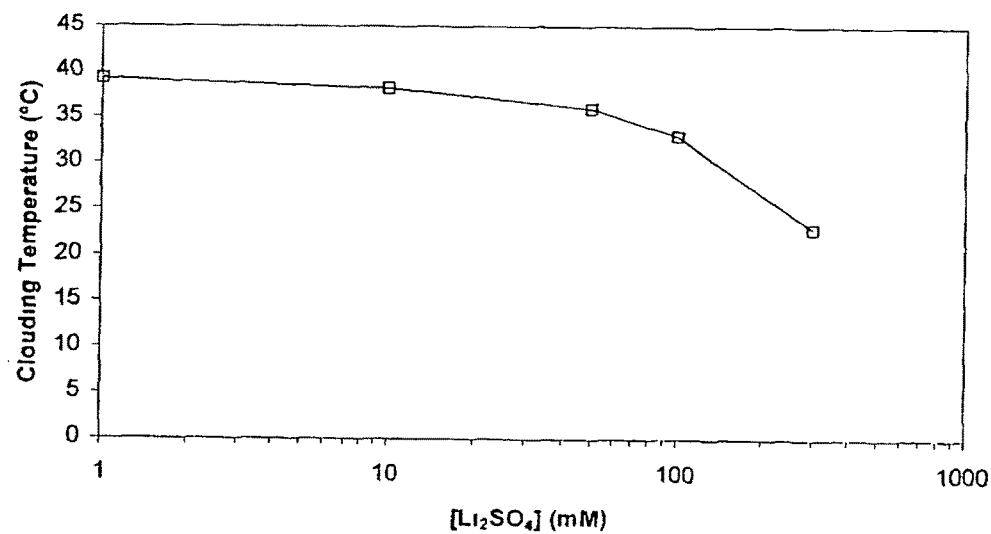
FIG. 4. Clouding temperatures for 0.1% (w/w) EHEC and $Li_2SO_4$ at pH 2.5. The clouding temperature of a 1M $Li_2SO_4$ and EHEC solution was determined to be less than 6° C. The cloud point found when increasing the temperature was determined to be approximately 1° C. higher than that found when decreasing the temperature.

The number-averaged particle sizes calculated for lipoplexes formulated using oxidized BFDMA were considerably smaller than lipoplexes formed using reduced BFDMA at all lipid concentrations investigated (Table 5). Although the exact reasons for this are not yet clear, these observations may result from differences in electrostatic interactions that result from the differences in the charge densities of reduced and oxidized BFDMA. For example, oxidized lipid, which has a net charge of +3, may bind and condense DNA more effectively than reduced lipid, which has a net charge of +1, at the same molar concentration. The sizes of lipoplexes prepared using oxidized lipid were measured to be small (e.g., 60 nm to 110 nm) at lower concentrations of oxidized lipid. These average sizes are sufficient for efficient internalization by endocytosis. However, levels of transfection were generally observed to be low using oxidized BFDMA (FIGS. 12 and 4). Larger aggregates were observed at a concentration of 20 $\mu$M oxidized BFDMA (ca. 610 nm). The average size of these aggregates falls outside the range generally considered optimal for endocytosis, but significantly higher levels of gene expression were observed at this lipid concentration relative to other lipid concentrations (FIGS. 12 and 14). As described earlier, it is possible that the larger aggregates formed at 20 $\mu$M could sediment more efficiently onto cells and that this could lead to enhanced internalization. It is also possible, however, that these differences in transfection could result from changes in the microstructures of the lipoplexes at this lipid concentration. Additional work will be required to evaluate these hypotheses more completely.

The intensity-averaged sizes calculated for aggregates formulated using reduced and oxidized BFDMA and diluted into serum-free media are also shown in Table 5. These intensity-averaged sizes were calculated from the same autocorrelation functions used to calculate the number-averaged sizes discussed above, and reveal trends similar to those observed for number-weighted average sizes. However, the intensity-weighted averages are larger than the number-weighted averages because light is scattered very strongly by the larger aggregates in solution.

G. Luciferase Expression in COS-7 Cells Exposed to Lipoplexes Formed from pCMV-Luc and Mixtures of Reduced and Oxidized BFDMA.

The inventors conducted transfection experiments with the COS-7 cell line using lipoplexes formed from a plasmid DNA construct (pCMV-Luc) encoding firefly luciferase and defined mixtures of reduced and oxidized BFDMA. Lipoplexes were prepared by fixing the total lipid concentration and varying the relative percentage of each oxidation state from 98% mole percent oxidized to 98% mole percent reduced. In a typical experiment, a solution of DNA (600 ng in 25 $\mu$L of water) was added to a vortexing solution of 1 mM aqueous $Li_2SO4$ (25 $\mu$L) containing an amount of BFDMA sufficient to give final total lipid concentrations of 6 $\mu$M when these formulations were added to cells in 200 $\mu$L of culture medium. The lipoplexes were incubated with cells for four hours, after which time the culture medium was removed and replaced with fresh medium. Gene expression was characterized after 48 hours by using a commercially available luminescence assay and resulting data are depicted in FIG. 17.

H. EGFP Expression in COS-7 Cells Exposed to Lipoplexes Formulated from A) pEGFP and Reduced BFDMA, B) pEGFP and Oxidized BFDMA, and C) pEGFP and BFDMA that was Oxidized and Subsequently Reduced Prior to being Contacted with DNA.

The inventors conducted experiments to demonstrate that BFDMA can be cycled electrochemically from the reduced state to the oxidized state and then back to the reduced state and retain the ability to transfect cells. In this experiment, BFDMA was oxidized at a potential of 500 mV. A portion of this oxidized sample was then reduced at a potential of −44 mV. The panels in FIG. 18 show fluorescence microscopy images collected from cells exposed to lipoplexes prepared from A) pEGFP and reduced BFDMA, B) pEGFP and oxidized BFDMA, and C) pEGFP and BFDMA that was oxidized and subsequently reduced prior to being contacted with DNA.

I. Demonstration of Structural and Biological Integrity of Nucleic Acid Following Exposure to Electrical Potential.

Referring to FIG. 19A, an agarose gel electrophoretic characterization of pEGFP following exposure to a reducing potential of −44 mV is shown. Lane 1 represents DNA that was not exposed to potential. Lanes 2 through 8 correspond to exposure times 5, 30, 60, 120, 180, 240, and 300 minutes, respectively. In FIG. 19B, luciferase expression in COS-7 cells transfected with CMV-Luc after exposure to −44 mV for the times indicated above. Following exposure to the reducing potential, DNA samples were formulated with Lipofectamine 2000 and exposed to COS-7 cells. The rightmost column corresponds to levels of transfection using a sample of naked DNA that was not exposed to an electrochemical potential.

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and encompassed by the following claims.

What is claimed is:

1. A method of controlling the aggregation of polymers by contact with redox active surfactants, comprising the step of contacting a polymer with a redox-active surfactant that is a cationic lipid transformable between oxidation states, wherein transforming the cationic lipid between oxidation states results in a change in charge density of said cationic lipid and the aggregation of the polymer is controlled by the oxidation state of said cationic lipid.

2. The method according to claim 1 wherein said polymer and redox-active surfactant are present in solution.

3. The method according to claim 1 wherein said redox-active surfactant bears a ferrocenyl moiety.

4. The method according to claim 1 wherein said polymer is a biopolymer.

5. The method according to claim 1 wherein said polymer is a nucleic acid, protein, polysaccharide, or derivative thereof.

6. A method for transfecting a cell, comprising the steps of:
(a) providing a redox active transfection agent in the form of a lipoplex between a nucleic acid and a redox active cationic lipid that is transformable between: (i) a first oxidation state that facilitates transfection of cells; and (ii) a second oxidation state that is less effective at transfecting cells, wherein transforming the cationic lipid between said first and second oxidation states results in a change in charge density of said cationic lipid; and
(b) contacting a cell with the redox-active transfection agent in which the cationic lipid is in said first oxidation state to facilitate transfection of the cell with the nucleic acid.

7. The method according to claim 6 further comprising the step of transforming the redox-active transfection agent to said first oxidation state.

8. The method according to claim 7 wherein the transforming step is carried out by applying an electrochemical potential to said redox-active transfection agent.

9. The method according to claim 8 wherein said electrochemical potential is provided by an electrode.

10. The method according to claim 7 wherein the transforming step is carried out by the transfer of electrons between said redox-active transfection agent and an electron donor/acceptor molecule.

11. The method according to claim 7 wherein the transforming step is carried out by exposure of the redox-active transfection agent to an oxidative/reductive environment of a tissue.

12. The method according to claim 11 wherein said tissue is a cancerous tissue.

13. The method according to claim 7 wherein the transforming step is spatially-controlled whereby said cell is selectively-transfected relative to a population of cells.

14. The method according to claim 7 wherein the transforming step is temporally-controlled whereby said cell is transfected at a predetermined time.

15. The method according to claim 6 wherein said method is carried out in vitro.

16. The method according to claim 6 wherein said method is carried out in vivo.

17. The method according to claim 6 wherein said redox-active cationic lipid further comprises a ferrocenyl moiety.

18. The method according to claim 6 wherein said redox-active transfection agent possesses an oxidation potential between about −2V to about +5V (vs. SCE).

19. A method for transfecting cells comprising steps of:
(a) providing a molecule containing a ferrocenyl moiety; and
(b) contacting a cell with a nucleic acid in the presence of the molecule containing the ferrocenyl moiety to facilitate transfection of the cell with the nucleic acid.

* * * * *